(12) United States Patent
Matono et al.

(10) Patent No.: US 11,331,273 B2
(45) Date of Patent: May 17, 2022

(54) FILM-COATED TABLET HAVING HIGH CHEMICAL STABILITY OF ACTIVE INGREDIENT

(71) Applicant: Intercept Pharmaceuticals, Inc., New York, NY (US)

(72) Inventors: Mitsuhiro Matono, Osaka (JP); Tetsuya Hayama, Osaka (JP)

(*) Notice: Subject to any disclaimer, the term of this patent is extended or adjusted under 35 U.S.C. 154(b) by 0 days.

(21) Appl. No.: 16/089,544

(22) PCT Filed: Mar. 30, 2017

(86) PCT No.: PCT/JP2017/013214
§ 371 (c)(1),
(2) Date: Sep. 28, 2018

(87) PCT Pub. No.: WO2017/170854
PCT Pub. Date: Oct. 5, 2017

(65) Prior Publication Data
US 2020/0268671 A1    Aug. 27, 2020

(30) Foreign Application Priority Data
Mar. 31, 2016   (JP) ............................. JP2016-071408

(51) Int. Cl.
*A61K 9/28* (2006.01)
*A61K 31/575* (2006.01)

(52) U.S. Cl.
CPC ............ *A61K 9/2826* (2013.01); *A61K 9/284* (2013.01); *A61K 9/2866* (2013.01); *A61K 31/575* (2013.01)

(58) Field of Classification Search
None
See application file for complete search history.

(56) References Cited

U.S. PATENT DOCUMENTS

| 4,522,840 | A * | 6/1985 | Corfield ................... A61K 9/28 427/2.17 |
| 2005/0080064 | A1 | 4/2005 | Pellicciari |
| 2010/0130426 | A1 * | 5/2010 | Young ...................... A61K 9/08 514/10.8 |
| 2011/0189245 | A1 * | 8/2011 | Terzian .................. A61K 9/286 424/400 |
| 2011/0311626 | A1 * | 12/2011 | Venkatesh ............... A61P 31/00 424/468 |
| 2013/0345188 | A1 * | 12/2013 | Steiner .................... A61P 31/14 514/182 |
| 2014/0186438 | A1 | 7/2014 | Manku et al. |
| 2016/0074419 | A1 | 3/2016 | Steiner et al. |
| 2016/0108082 | A1 * | 4/2016 | Steiner ................... A61K 31/00 552/553 |

FOREIGN PATENT DOCUMENTS

| CN | 106974916 A | 1/2016 | |
| CN | 107188917 A | 3/2016 | |
| CN | 106046094 A | 10/2016 | |
| TR | 201410001 A * | 8/2014 | |
| WO | WO 2006/011637 A1 | 2/2006 | |
| WO | WO-2006011637 A1 * | 2/2006 | ............. A61K 9/282 |
| WO | WO 2013/192097 A1 | 12/2013 | |
| WO | WO 2016/176208 A1 | 11/2016 | |

OTHER PUBLICATIONS

Anonymous: "Opadry amb II", High Performance Moisture Barrier Film Coatings, Mar. 1, 2016, pp. 1-4. Retrieved from the Internet: URL:https://www.colorcon.com/products-formulation/all-products/46-opadry-amb-ii/2003-opadry-amb-ii-product-information-brochure [retrieved on Oct. 21, 2019].

Shen E. "CoverUp", Innovations in Pharmaceutical Technology, Issue 52, 2015, p. 44-47.

Kitagawa, Shuji, ed. "8 Hoshutsu Seigyogata Seizai", Basic Yakugaku Kyokasho Series 20 Yakuzaigaku (2nd edition, 2nd print), 2013, p. 169-175 (English translation provided).

Miyajima, Masaharu et al., Chapter 1 Jozai Capsule-zai ni Shiyo sareru Tenkazai, Formulation Design and Physicochemical Characterization for Pharmaceutical Excipients, 2016, p. 3-18 (English translation provided).

Yamauchi, Hitoshi et al., "Nyumon Koza Iyakuhin Bun'ya ni Okeru Kaimen Kasseizai", Oleoscience, 2002, vol. 2, No. 11, p. 697-704 (English translation provided).

English translation of the foreign application WO 2006/011637 A1 (10 pages).

* cited by examiner

*Primary Examiner* — Melissa S Mercier

(57) ABSTRACT

The present invention relates to a film-coated tablet having a high chemical stability of an active ingredient, said film-coated tablet comprising: (a) a tablet core containing obeticholic acid or a pharmaceutically acceptable salt thereof; and (b) a coating layer, which is provided on the surface of the tablet core, containing a film base and being substantially free from any plasticizer or containing at least one kind of specific plasticizer.

13 Claims, No Drawings

FILM-COATED TABLET HAVING HIGH CHEMICAL STABILITY OF ACTIVE INGREDIENT

TECHNICAL FIELD

The present invention relates to a film-coated tablet having high active ingredient chemical stability which contains as an active ingredient the FXR agonist obeticholic acid or a pharmaceutically acceptable salt thereof, wherein proliferation of obeticholic acid dimers which are readily generated impurity, is inhibited.

BACKGROUND ART

Obeticholic acid (also known as INT-747 or DSP-1747), represented by the chemical formula shown below, is a ligand that activates the farnesoid X receptor (FXR)—i.e., a compound which pharmacologically acts as an FXR agonist—which has shown promise for use in the treatment of NASH, PBC, etc. (Patent Documents 1 and 2).

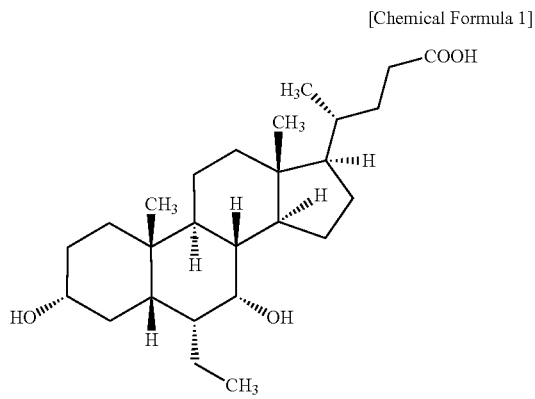

[Chemical Formula 1]

Patent Document 1 discloses that oral administration of obeticholic acid compounds is preferable for the prevention and treatment of FXR-mediated disease and symptoms, with examples of oral formulations given including tablets, capsules, wafer capsules and lozenges, but it does not provide any disclosure regarding a film-coated tablet containing obeticholic acid.

Patent Document 2 discloses a tablet formulation containing 1 to 25 mg of obeticholic acid, with each tablet containing 1 to 25 mg obeticholic acid, 157 to 185 mg microcrystalline cellulose, 12 mg sodium starch glycolate, 2 mg magnesium stearate, 4 mg colloidal silicon dioxide and 8 mg coating material (Opadry II®); that is, said document discloses a specific film-coated tablet. Additionally, the document discloses that crude obeticholic acid contains obeticholic acid dimers (referred to as "Impurity 6", "3α (3α,7α-dihydroxy-6α-ethyl-5β-cholan-24-oyloxy)-7α-hydroxy-6α-ethyl-5β-3-cholan-24-oic acid", and "6 ECDCA dimer" in Patent Document 2) as one of several impurities generated during the manufacturing process.

In recent years, medical institutions such as hospitals and dispensing pharmacies have come to actively employ a medication adherence improvement scheme whereby different medications taken by a single patient for a given time period are placed in a single package in order to prevent repeat or erroneous administration, sometimes referred to as "single package dispensing", and said scheme is currently considered particularly important in the medical field in Japan. As a result, for a certain period of time extending from when a prescribed drug is removed from its original packaging or PTP sheet until the patient takes the drug, the drug may be exposed to humid conditions which are not optimal for storage. Given the above background and medical needs, there is currently a strong desire within the medical field for an oral preparation which shows excellent active ingredient chemical stability, wherein the oral preparation will not degrade or deteriorate due to decomposition, etc., even when stored under excessively humid conditions (e.g., under severe test conditions such as open conditions: 40° C., 75% RH (relative humidity)).

PRIOR ART DOCUMENTS

Patent Documents

Patent Document 1 JP 4021327 B2
Patent Document 2 WO 2013/192097 (JP 2015-52162 A)

SUMMARY OF THE INVENTION

Problem which the Invention Seeks to Solve

The objective of the present invention is the provision of a film-coated tablet having high active ingredient chemical stability which contains as an active ingredient obeticholic acid or a pharmaceutically acceptable salt thereof. More specifically, the objective is the provision of a film-coated tablet containing obeticholic acid which inhibits the ready generation and significant proliferation of obeticholic acid dimers which constitute a readily generated impurity of obeticholic acid.

Means for Solving the Problem

Upon diligent investigations intended to solve the aforementioned problem, the inventors discovered that the problem could be solved by the following means.

Specifically, the invention is as follows.
[1] A film-coated tablet containing obeticholic acid or a pharmaceutically acceptable salt thereof, which contains:
(a) an uncoated tablet containing obeticholic acid or a pharmaceutically acceptable salt thereof, and
(b) a film base on the surface of said uncoated tablet, and which has a coating layer which either does not substantially contain a plasticizer or which contains at least one type of specific plasticizer selected from a group consisting of: triethyl citrate, lecithin, glycerin fatty acid ester, propylene glycol, triacetin, polyoxyethylene sorbitan fatty acid ester, concentrated glycerin, sorbitan fatty acid ester, sorbitol, glycerin, diethyl phthalate, dibutyl sebacate, tributyl citrate, diethyl sebacate, acetylated monoglyceride, acetyl triethyl citrate, acetyl tributyl citrate, monostearin, dioctyl phthalate, butyl phthalyl butyl glycolate and medium chain fatty acid triglycerides.
[2] A film-coated tablet as specified in [1], which has a coating layer which does not substantially contain a plasticizer.
[3] A film-coated tablet as specified in [1] which has a coating layer which contains at least one type of specific plasticizer selected from a group consisting of: triethyl citrate, lecithin, glycerin fatty acid ester, propylene glycol, triacetin, polyoxyethylene sorbitan fatty acid ester, concentrated glycerin, sorbitan fatty acid ester, sorbitol, glycerin, diethyl phthalate, dibutyl sebacate, tributyl citrate, diethyl sebacate, acetylated monoglyceride, acetyl triethyl citrate, acetyl tributyl citrate, monostearin, dioctyl phthalate, butyl phthalyl butyl glycolate and medium chain fatty acid triglycerides.
[4] A film-coated tablet as specified in either [1] or [3], wherein the specific plasticizer is selected from a group consisting of triethyl citrate, lecithin, glycerin fatty acid ester, propylene glycol, triacetin, polyoxyethylene sorbitan fatty acid ester, concentrated glycerin and sorbitan fatty acid ester.

[5] A film-coated tablet as specified in any of [1], [3] and [4], wherein the sorbitan fatty acid ester is sorbitan sesquioleate or sorbitan monolaurate.

[6] A film-coated tablet as specified in any of [1] and [3] to [5], wherein the sorbitan fatty acid ester is sorbitan sesquioleate.

[7] A film-coated tablet as specified in any of [1] and [3] to [6], wherein the specific plasticizer is selected from a group consisting of triethyl citrate, lecithin, glycerin fatty acid ester, propylene glycol, triacetin and polyoxyethylene sorbitan fatty acid ester.

[8] A film-coated tablet as specified in any of [1] and [3] to [7], wherein the glycerin fatty acid ester is glyceryl monostearate.

[9] A film-coated tablet as specified in any of [1] and [3] to [8], wherein the specific plasticizer is selected from a group consisting of triethyl citrate, propylene glycol, triacetin and polyoxyethylene sorbitan fatty acid ester.

[10] A film-coated tablet as specified in any of [1] and [3] to [9], wherein the polyoxyethylene sorbitan fatty acid ester is polyoxyethylene sorbitan monooleate.

[11] A film-coated tablet as specified in any of [1] and [3] to [10], wherein the specific plasticizer is selected from a group consisting of triethyl citrate, propylene glycol and triacetin.

[12] A film-coated tablet as specified in any of [1] and [3] to [11], wherein the specific plasticizer is triethyl citrate.

[13] A film-coated tablet as specified in any of [1] and [3] to [12], wherein the amount of specific plasticizer included is 0.1 to 30% by weight.

[14] A film-coated tablet as specified in [1] or [2], wherein a coating layer which does not substantially include a plasticizer includes at least one type of film base selected from a group consisting of hydroxypropyl methyl cellulose, hydroxypropyl cellulose, methyl cellulose, ethyl cellulose, polyvinyl alcohol-based resin, polyvinyl pyrrolidone and methacrylic acid copolymer.

[15] A film-coated tablet as specified in any of [1], [2] and [14], wherein a coating layer which does not substantially include a plasticizer includes at least one type of film base selected from a group consisting of hydroxypropylmethyl cellulose and polyvinyl alcohol-based resin.

[16] A film-coated tablet as specified in [14] or [15], wherein the polyvinyl alcohol-based resin is any of polyvinyl alcohol, a polyvinyl alcohol derivative, a polyvinyl alcohol copolymer or a mixture thereof.

[17] A film-coated tablet as specified in any of [14] to [16], wherein the polyvinyl alcohol-based resin is polyvinyl alcohol.

[18] A film-coated tablet as specified in any of [1], [2], [14] and [15], wherein a coating layer which does not substantially include a plasticizer includes a hydroxypropylmethyl cellulose film base.

[19] A film-coated tablet as specified in any of [1], [2] and [14] to [18], wherein the amount of film base included is 30 to 100% of the coating layer by weight.

[20] A film-coated tablet as specified in any of [1] and [3] to [13], wherein a coating layer which includes at least one type of the aforementioned specific plasticizer includes at least one type of film base selected from a group consisting of hydroxypropyl methyl cellulose, hydroxypropyl cellulose, methyl cellulose, ethyl cellulose, polyvinyl alcohol-based resin, polyvinyl pyrrolidone and methacrylic acid copolymer.

[21] A film-coated tablet as specified in any of [1], [3] to [13] and [20], wherein a coating layer which includes at least one type of the aforementioned specific plasticizer includes at least one type of film base selected from a group consisting of hydroxypropylmethyl cellulose and polyvinyl alcohol-based resin.

[22] A film-coated tablet as specified in [20] or [21], wherein the polyvinyl alcohol-based resin is any of polyvinyl alcohol, a polyvinyl alcohol derivative, a polyvinyl alcohol copolymer or a mixture thereof.

[23] A film-coated tablet as specified in any of [20] to [22], wherein the polyvinyl alcohol-based resin is polyvinyl alcohol.

[24] A film-coated tablet as specified in any of [1], [3] to [13], [20] and [21], wherein a coating layer which includes at least one type of the aforementioned specific plasticizer includes a hydroxypropylmethyl cellulose film base.

[25] A film-coated tablet as specified in any of [20] to [24], wherein the amount of film base included is 30 to 98% of the coating layer by weight.

Advantageous Effects of the Invention

Specifically, for the application of single package dispensing which is needed to improve medication adherence, which is strongly desired in the medical field, the design of an oral preparation which demonstrates superior active ingredient chemical stability even when stored under humid conditions (e.g., under severe test conditions such as open conditions: 40° C., 75% RH (relative humidity)) is required.

The results of an investigation conducted by the inventors of the present invention showed that tablets which contain obeticholic acid as disclosed in Patent Document 2 are particularly susceptible to generating, and show a significant increase in, obeticholic acid dimers which have been disclosed as one type of impurity originating from the crude drug material when said tablets are stored under open conditions at 40° C. and 75% RH. It should be noted that obeticholic acid dimers are known as a type of very readily produced impurity which is generated and proliferates if in relatively minute amounts even when obeticholic acid is stored under similar conditions entirely as a crude drug material. In order to reliably respond to single package dispensing needs, it is necessary to suppress the significant increase in readily generated obeticholic acid dimer impurities which can occur in drug preparations. That is, the discovery of an oral preparation showing superior chemical stability for obeticholic acid which makes it possible to further suppress obeticholic acid dimer proliferation beyond the preparations disclosed in Patent Document 2 constituted an important problem tackled by the present invention.

Additionally, according to ICH guidelines and the Q3B "Guidelines on Impurities in Pharmaceuticals Containing Novel Active Ingredients," the threshold value which is needed to confirm the safety of the degradation products of a new formulation depends on the maximum daily dose of the novel active ingredient, and, for example, when the maximum daily dosage for a novel active ingredient is 10 mg to 100 mg, "0.5% or 200 g total daily intake, whichever is lower" is regarded as a suitable threshold. In order to comply with these guidelines, it is of course preferable to reduce the production of decomposition products to the greatest extent possible, and taking into consideration the actual expiration date of pharmaceutical preparations provided in clinical practice, more specifically a decomposition product concentration which does not exceed 0.5% even when stored under humid conditions (e.g., under severe test conditions such as open conditions: 40° C., 75% RH (relative humidity) sustained for, for example, 1 month (1M) or 3 months (3M)) is used as a realistic and practical rule of thumb. In other words, in the context of the present invention, one specific problem was the limitation of the production of the primary decomposition product obeticholic acid dimer in the aforementioned obeticholic acid preparation to less than 0.5% under the above conditions.

The inventors of the present invention conducted extensive studies to solve the above problem and in doing so discovered that a certain general purpose plasticizer (polyethylene glycol) which typically serves as a film base for stabilizing active ingredients was responsible for promoting the proliferation of obeticholic acid dimers in the pharmaceutical preparation disclosed in Patent Document 2. Further investigations were also made regarding film coating components, and it was determined that a pharmaceutical preparation according to the present invention which was characterized in that it comprised a film coating component different from the pharmaceutical preparation disclosed in Patent Document 2 and in that it did not substantially use a plasticizer or that it used a specific kind of plasticizer is capable of limiting the generation and proliferation of obeticholic acid dimers. The present invention has made it possible to provide an oral preparation, and, in particular, a film-coated tablet, which includes as an active ingredient obeticholic acid and which demonstrates superior chemical stability for said active ingredient. In a preferred embodiment of the present invention, even when stored under humid conditions (e.g., 40° C. and 75% RH, open for 1 M or 3 M) readily produced impurities (primary decomposition products) which are obeticholic acid dimers in preparations of obeticholic acid can be limited to less than 0.5%.

The film-coated tablet according to the present invention demonstrates a level of stability that is significantly better than film-coated tablets containing a typical plasticizer. Therefore, the film-coated tablet according to the present invention can be stored in a state where it is not individually packaged (e.g., PTP packaging, etc.), making so-called bulk packaging also possible. Therefore, the film-coated tablet according to the present invention can be prescribed to the patient in the form of a simple package (e.g., packaged with glassine paper, drug packaging paper) or one dose package for each administration time point.

MODE OF EMBODIMENT OF THE INVENTION

The present invention is described in further detail below.

The first embodiment of the present invention is a film-coated tablet which has a coating layer (hereafter referred to as a film coating, film coating membrane, film coating layer or simply as a coating layer) which does not substantially include a plasticizer and which includes a film base on the surface of an uncoated tablet which contains obeticholic acid or a pharmaceutically acceptable salt thereof. The aforementioned film-coated tablet demonstrates an advantage in that degradation of the active ingredient obeticholic acid is limited and/or the production of the readily generated impurity obeticholic acid dimer is limited even when it is stored for a long time without protective packaging such as aluminum packaging.

For the film-coated tablet for which a film coating has been applied, a general purpose plasticizer is included in a typical film coating and said general purpose plasticizer is typically considered to be not readily reactive with the active ingredient or the film coating itself is considered more generally capable of stabilizing the active ingredient. This is because for a film-coated tablet, the active ingredient contained in the uncoated tablet is only in two-dimensional contact with the general-purpose plasticizer contained in the film coating at a very limited part, namely the interface of the two elements, and within the uncoated tablet the two elements are not in a state whereby they are in mixed contact in a three dimensional configuration, and the film coating layer functions as a protective film covering the outer part, preventing ingress of moisture or light to the uncoated tablet portion. However, according to an investigation conducted by the inventors of the present invention it is surprisingly a general use plasticizer—more specifically, polyethylene glycol—contained in the film coating layer which typically should contribute to the stability of the active ingredient, which promotes proliferation of obeticholic acid dimers as described above. It was determined that contact between the general purpose plasticizer (polyethylene glycol) included in the film coating of said pharmaceutical preparation and the obeticholic acid contained in the uncoated tablet at the extremely limited interface between said two elements as described above surprisingly significantly promoted the generation of obeticholic acid dimers. Specifically, it was determined that, for example, as shown in the following examples (Comparative Examples 1 and 2), under humid conditions (e.g., 40° C. and 75% RH, open for 1 M or 3 M) a pharmaceutical preparation which contained obeticholic acid in the uncoated tablet as well as the aforementioned general purpose plasticizer (polyethylene glycol) in the film coating showed generation of obeticholic acid dimers at a level which greatly exceeded the reference value (e.g., 0.5%).

Based on the above discovery, the inventors of the present invention determined that when coating is performed using a coating layer which does not substantially include plasticizer which is typically included in a covering layer (film coating) the production of obeticholic acid dimers is inhibited even during long-term storage (first embodiment). More specifically, for example as shown in the following examples, film-coated tablets produced by covering an uncoated tablet which contains obeticholic acid with a coating layer which does not include plasticizer show inhibition of obeticholic acid dimer generation to less than the reference value (e.g., 0.5%) even under harsh high-humidity conditions (e.g., 40° C. and 75% RH, open for 1 M or 3 M).

Additionally, the inventors of the present invention also determined via further study that there exists a specific preferred plasticizer which inhibits the generation of obeticholic acid dimers.

The second embodiment of the present invention is a film-coated tablet which has a coating layer which includes at least one type of specific plasticizer and which includes a film base on the surface of an uncoated tablet which contains obeticholic acid or a pharmaceutically acceptable salt thereof. For the aforementioned film-coated tablet, a specific preferred plasticizer discovered by the inventors of the present invention (referred to as the "specific plasticizer" in this specification) is added to the coating layer, thereby ensuring that the coating process can be performed smoothly and plasticity is conferred to the film coating membrane such that peeling of the film on the film-coated tablet is reduced and degradation of the active ingredient obeticholic acid is limited and/or the production of the readily generated impurity obeticholic acid dimer is limited even when it is stored for a long time without protective packaging such as aluminum packaging. As far as the chemical stability of the active ingredient is concerned, more specifically, for example as shown in the following examples, film-coated tablets produced by covering an uncoated tablet which contains obeticholic acid with a coating layer which includes a specific plasticizer show inhibition of obeticholic acid dimer generation to less than the reference value (e.g., 0.5%) even under harsh high-humidity conditions (e.g., 40° C. and 75% RH, open for 1 M or 3 M).

Additionally, the second embodiment of the invention, which ensures the aforementioned coating process can be performed smoothly while limiting film peeling, etc., and which does not impede production, is a more preferable embodiment compared to the first embodiment described above.

Active Ingredient
(a) Obeticholic Acid or a Pharmaceutically Acceptable Salt Thereof As used in the present specification, "obeticholic acid" refers to a compound having the following chemical structure.

[Chemical Formula 2]

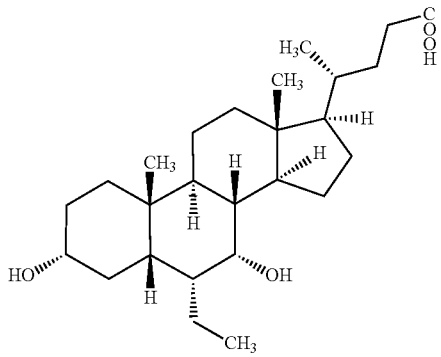

Other chemical names, names, and abbreviations of obeticholic acid include 6-α-ethyl-3α,7α-dihydroxy-5β-cholan-24-oic acid, 3α,7α-dihydroxy-6α-ethyl-5β-cholan-24-oic acid, 6α-ethylchenodeoxycholic acid, 6-ethyl-CDCA, 6ECDCA, cholan-24-oic acid, 6-ethyl-3,7-dihydroxy-(3α,5,6α,7α)-, OCA, DSP-1747, and INT-747. The CAS registration number of obeticholic acid is 459789-99-2. This term encompasses all forms of obeticholic acid (e.g., amorphous, crystalline, and various crystal polymorphisms).

In the context of the present invention, obeticholic acid is treated as an acidic compound, and examples of "pharmaceutically acceptable salts of obeticholic acid" include inorganic salts (such as sodium, potassium, lithium, barium, calcium, and magnesium salts) and organic salts (such as pyridinium, picolinium, and triethylammonium salts).

Additionally, in the context of the present invention, obeticholic acid or pharmaceutically acceptable salts thereof include solvates thereof. Examples of solvents that can be used to form solvates include, but are not limited to, water as well as pharmaceutically acceptable organic solvents such as ethanol, acetone, ethyl acetate, and hexane.

In the context of the present invention, obeticholic acid (free form) is particularly preferred as obeticholic acid or a pharmaceutically acceptable salt thereof. In the context of the present invention, amorphous obeticholic acid (also referred to as amorphous or non-crystalline form) is particularly preferred.

In the context of the present invention, obeticholic acid or a pharmaceutically acceptable salt thereof may be milled to a desired particle size before the particles are produced, as needed. Milling is performed via common methods such as milling using a pulverizing mill and extremely fine particles may also be used. For example, the diameter of particles representing ≥90% of particles by volume (D90) may be ≤100 μm, and average particle diameter by volume (50% particle size: D50) may range, for example, from 0.1 to 20 μm, or, preferably, from 1 to 10 μm. When the preparation is in the form of tablets, the amount of obeticholic acid or pharmaceutically acceptable salt thereof added, based on total tablet weight, may be selected, for example, from within a range of 0.1 to 50% by weight, or, preferably, from within a range of 1 to 30% by weight, and a range of 3 to 20% by weight is particularly preferred. Additionally, when the preparation is in the form of tablets, for example the amount of obeticholic acid or pharmaceutically acceptable salt thereof included per tablet may range from 0.1 to 160 mg, 1 to 80 mg, or, preferably, 2.5 to 40 mg or 2.5 to 50 mg, with ranges of 2.5 to 20 mg, 5 to 20 mg, 2.5 to 25 mg and 5 to 25 mg particularly preferred. Alternatively, tablets may be in the form of, for example, 1 mg tablets, 1.25 mg tablets, 2 mg tablets, 2.5 mg tablets, 5 mg tablets, 10 mg tablets, 12.5 mg tablets, 20 mg tablets, 25 mg tablets, 40 mg tablets, 50 mg tablets, 80 mg tablets, or 100 mg tablets, with 2.5 mg tablets, 5 mg tablets, 10 mg tablets, 20 mg tablets, 25 mg tablets, 40 mg tablets and 50 mg tablets preferable. In particular, 25 mg tablets are preferred.

Readily Generated Impurities

"Obeticholic acid dimer" refers to any compound having the following chemical structure.

[Chemical Formula 3]

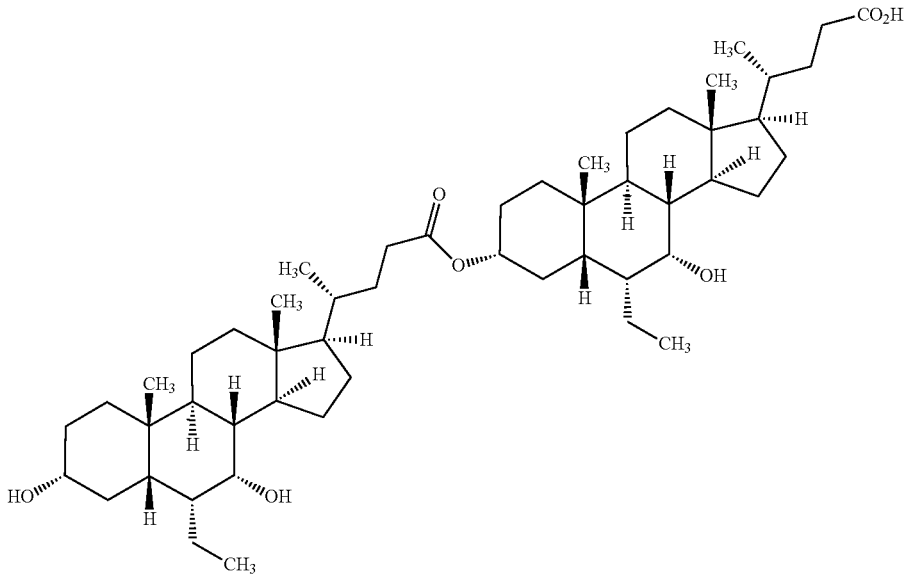

Patent Document 2 (JP 2015-52162 A) given above discloses a method for the production of obeticholic acid and also discloses that crude obeticholic acid produced via said method contains obeticholic acid dimers (referred to as "Impurity 6", "3α (3a, 7α-dihydroxy-6α-ethyl-5β-cholan-24-oyloxy)-7α-hydroxy-6α-ethyl-5β-cholan-24-oic acid", and "6 ECDCA dimer" in Patent Document 2) as one of six impurities generated during the manufacturing process. The fact that said impurity is generated readily (i.e., a readily generated impurity) during the storage as well as preparation of crude drug and pharmaceutical preparations has not been previously disclosed and was first discovered by the inventors of the present invention as a problem to be solved by the present invention.

Covering Layer (Film Coating)

Film Coating Agent

The tablet according to the present invention is characterized in that it is subject to a specific film coating—i.e., a specific coating layer is formed. Tablets subject to said film coating (for which a coating layer is formed) are referred to as film-coated tablets (also referred to as FC tablets in the description of the present application). Film coating agents used for the film coating generally include those combining a film base such as hypromellose, hydroxypropyl cellulose, polyvinyl pyrrolidone, polyvinyl alcohol-based resins (including polyvinyl alcohols, polyvinyl alcohol derivatives and polyvinyl alcohol copolymers), methacrylic acid copolymer L, methacrylic acid copolymer LD, methacrylic acid copolymer S, aminoalkyl methacrylate copolymer RS, or ethyl acrylate-methyl methacrylate copolymer, and a plasticizer such as polyethylene glycol, propylene glycol, triacetin, triethyl citrate, glycerin or glycerin fatty acid ester.

In the context of the present invention, "plasticizer" refers to an additive which imparts flexibility by imparting plasticity to a material, and generally refers to all plasticizers in common use. For example, plasticizer refers to an additive with the "plasticizer" designation under "applications" in the 2007 Pharmaceutical Additives Dictionary with specific examples including dioctyl adipate, adipic acid polyester, epoxidized soybean oil, epoxyhexahydrophthalic acid diester, Karion 83, triethyl citrate, glycerin, glycerin fatty acid ester, sesame oil, vinyl acetate resin, dimethylpolysiloxane/silicon dioxide mixtures, D-sorbitol, medium chain fatty acid triglycerides, sugar alcohol solutions derived from corn starch, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, polysorbate 80, polyethylene glycol (examples of polyethylene glycol include Macrogol 400, Macrogol 600, Macrogol 1500, Macrogol 4000, Macrogol 6000, etc.), isopropyl myristate, cottonseed oil/soybean oil mixtures, glyceryl monostearate, isopropyl linoleate, liquid paraffin, etc.

"Does not contain a plasticizer" indicates that none of the aforementioned plasticizers or the following specific plasticizers are included in the coating layer.

"Does not substantially contain a plasticizer" indicates that no plasticizer is included in the coating layer, or the amount included is not sufficient to function as a plasticizer in general or does not confer plasticity to the coating layer. More specifically, the amount of plasticizer included in the coating layer corresponding to "does not substantially contain plasticizer" (upper limit) is, for example, less than 1% by weight, preferably less than 0.1% by weight.

The present invention is characterized in that the use of a specific plasticizer as described below is preferred and a film base as described below is preferred.

(b) Specific Plasticizer

Examples of the "specific plasticizer" include triethyl citrate, lecithin, glycerin fatty acid ester, propylene glycol, triacetin, polyoxyethylene sorbitan fatty acid ester, concentrated glycerin, sorbitan fatty acid ester, sorbitol, glycerin, diethyl phthalate, dibutyl sebacate, tributyl citrate, diethyl sebacate, acetylated monoglyceride, acetyl triethyl citrate, acetyl tributyl citrate, monostearin, dioctyl phthalate, butyl phthalyl butyl glycolate and medium chain fatty acid triglycerides. These compounds are generally included in pharmaceutical preparations as plasticizers. Additionally, some of these compounds are included in preparations as emulsifiers, dispersants, brighteners, stabilizers, surfactants, etc.

Thus, at least one type of specific plasticizer, more specifically at least one component selected from a group consisting of triethyl citrate, lecithin, glycerin fatty acid ester (including glyceryl monostearate), propylene glycol, triacetin, polyoxyethylene sorbitan fatty acid ester (including polyoxyethylene sorbitan monooleate), concentrated glycerin, sorbitan fatty acid ester (including sorbitan sesquioleate and sorbitan monolaurate), sorbitol, glycerin, diethyl phthalate, dibutyl sebacate, tributyl citrate, diethyl sebacate, acetylated monoglyceride, acetyl triethyl citrate, acetyl tributyl citrate, monostearin, dioctyl phthalate, butyl phthalyl butyl glycolate and medium chain fatty acid triglycerides should preferably be included in the coating layer. By doing so, generation of obeticholic acid dimers is further inhibited and, compared to when a plasticizer is not used, coating at the time of production is performed smoothly and plasticity is conferred onto the coating layer, thereby limiting peeling of the film on the film-coated tablet. Preferable examples include triethyl citrate, lecithin, glycerin fatty acid ester (including glyceryl monostearate), propylene glycol, triacetin, polyoxyethylene sorbitan fatty acid ester (including polyoxyethylene sorbitan monooleate), concentrated glycerin, sorbitan fatty acid ester (including sorbitan sesquioleate and sorbitan monolaurate), while triethyl citrate, lecithin, glycerin fatty acid ester (including glyceryl monostearate), propylene glycol, triacetin, polyoxyethylene sorbitan fatty acid ester (including polyoxyethylene sorbitan monooleate) are more preferable, triethyl citrate, propylene glycol, triacetin, polyoxyethylene sorbitan fatty acid ester (including polyoxyethylene sorbitan monooleate) are yet more preferable and triethyl citrate, propylene glycol and triacetin are particularly preferable.

The glycerin fatty acid ester specified above is not limited in any particular way provided it is a fatty acid ester of glycerin, with examples including glyceryl monolaurate, glyceryl monomyristate, glyceryl monopalmitate, glyceryl monostearate, glyceryl monooleate, etc., and glyceryl monostearate is particularly preferable. The polyoxyethylene sorbitan fatty acid ester specified above is not limited in any particular way provided it is a fatty acid ester of polyoxyethylene sorbitan, with examples including polyoxyethylene sorbitan monolaurate, polyoxyethylene sorbitan monomyristate, polyoxyethylene sorbitan monopalmitate, polyoxyethylene sorbitan monostearate, polyoxyethylene sorbitan monooleate, etc., and polyoxyethylene sorbitan monooleate (also referred to as polysorbate 80) is particularly preferable. The sorbitan fatty acid ester specified above is not limited in any particular way as long as it is a fatty acid ester of sorbitan, and examples thereof include sorbitan sesquioleate, sorbitan monolaurate, sorbitan monomyristate, sorbitan monopalmitate, sorbitan monostearate, sorbitan monooleate, and sorbitan sesquioleate and sorbitan monolaurate are preferable, and sorbitan sesquioleate is particularly preferable.

The amount of the above plasticizer(s) included in the coating layer ranges from, for example, 0.1 to 30% by weight, with a range of 1-25% by weight preferred and a range of 1 to 15% by weight particularly preferred.

The following section provides examples of components which may be contained in a coating layer which does not (substantially) contain the aforementioned plasticizer(s) as well as components contained in a coating layer other than the specified plasticizer(s).

(c) Film Base

Examples of film bases include cellulose derivatives such as hydroxypropylmethylcellulose (HPMC), hydroxypropylcellulose (HPC), methylcellulose (MC), ethylcellulose (EC), etc., vinyl polymers such as polyvinyl alcohol (PVA) based resin, polyvinyl pyrrolidone (PVP), etc., and acrylic polymers such as methacrylic acid copolymer, etc. Preferable examples include hydroxypropylmethyl cellulose and a polyvinyl alcohol-based resin (including polyvinyl alcohols, polyvinyl alcohol derivatives and polyvinyl alcohol copolymers), even more preferable examples include hydroxypropyl methyl cellulose and polyvinyl alcohol, and yet more preferable examples include hydroxypropylmethyl cellulose. For a coating layer which does not include plasticizer or a coating layer which does not substantially include plasticizer, the concentration of film base in the coating layer ranges from approximately 5 to approximately 100% by weight, with approximately 30 to approximately 100% by weight preferable and approximately 30 to 98% by weight particularly preferable. Furthermore, for a coating layer which includes a specific plasticizer, the concentration ranges from approximately 5 to approximately 99.9% by weight, with approximately 30 to approximately 98% by weight preferable and approximately 30 to approximately 93% by weight particularly preferable.

Polyvinyl alcohol-based resins refer to polyvinyl alcohol (PVA), polyvinyl alcohol derivatives, and polyvinyl alcohol copolymers, and commercially available types can generally be used. Examples of specific commercially sold polyvinyl alcohol preparations include Gohsenol® EG-03P, EG-05P, EG-18P, EG-22P, EG-30P, EG-40P, EG-48P, EG-05PW, EG-30PW and EG-40 PW. Examples of specific commercially sold polyvinyl alcohol copolymer preparations include Kollicoat® IR, a polyvinyl alcohol-polyethylene glycol graft copolymer produced by BASF. Examples of specific commercially sold polyvinyl alcohol derivative preparations include the polyvinyl alcohol copolymers POVACOAT® Type F, Type R, and Type L produced by Daido Chemical Corporation.

Polyvinyl alcohol is usually produced by polymerizing vinyl acetate, which is then completely or partially saponified. Polyvinyl alcohol as specified in the Japan Pharmaceutical Excipient Standards, for example, can be used in the present invention; fully saponified products are defined as having a degree of polymerization of at least 97 mol %, whereas partially saponified products are defined as having a degree of polymerization of 79 to 96 mol %. The degree of saponification of the polyvinyl alcohol used in the present invention is not subject to any particular limitations, but the use of partially saponified products is preferred. The viscosity of the polyvinyl alcohol used in the present invention is also not particularly limited, but viscosity at 20° C. in a 4% by weight aqueous solution preferably ranges from 2 to 40 mPa·s, with a range of 3 to 30 mPa·s more preferable, a range of 4 to 20 mPa·s yet more preferable and a range of 4.5 to 6 mPa·s most preferable. The viscosity is the value that is determined by the method described in the Japanese Pharmacopoeia Sixteenth Edition, General Tests, Processes and Apparatus, 2.53 Viscosity Determination, Method 1: Viscosity measurement by capillary tube viscometer.

Examples of components that may be added to the coating layer other than the film base and the specific plasticizer include, for example, colouring agents such as Litanium oxide and iron sesquioxide (concentration in coating layer: approximately 0.1 to approximately 50% by weight), anti-sticking agents such as talc (concentration in coating layer: approximately 0.1 to approximately 50% by weight), brighteners such as anhydrous silicic acid and carnauba wax (concentration in coating layer: approximately 0.01 to approximately 10% by weight), etc. Additionally, a plasticizer may be added as appropriate when necessary.

The coating layer can be formed by spraying a liquid composition (coating liquid) prepared by selecting and dissolving or suspending one or two or more types of film base (or film base as well as specific plasticizer) as specified above into water or an organic solvent such as ethanol (preferably, water) onto an uncoated tablet. Additionally an aforementioned colouring agent, anti-sticking agent, brightener, etc. may be blended into the coating liquid as necessary.

Examples of equipment include devices classified as coating pans. Preferred examples include devices classified as perforated coating systems.

Uncoated Tablet

An "uncoated tablet" may be obeticholic acid or a pharmaceutically acceptable salt thereof alone, but it will generally be prepared by blending in other pharmaceutical ingredients (additives). These additional ingredients may be used as long as they do not cause any problems and are required for the formulation of the tablet. Examples of the above include excipients, binders, disintegrants, lubricants, etc.

Preferred examples are given below, but, as stated above, the primary distinguishing characteristics of the present invention lie in the coating layer and the components of the uncoated tablet (uncoated tablet section) and are in no way limited to the following examples.

(d) Excipient

Specific examples of excipients include sugar or sugar alcohols, crystalline cellulose, anhydrous calcium hydrogen phosphate, calcium hydrogen phosphate, calcium carbonate and calcium sulfate with sugar or sugar alcohol preferred. Said excipients can be used alone or in a combination of two or more.

Examples of sugars and sugar alcohols include, but are not limited to, mannitol, erythritol, xylitol, maltitol, sorbitol, lactose, sucrose, and trehalose. Mannitol, erythritol, lactose, and trehalose are preferred, mannitol, erythritol, and lactose are more preferred, mannitol and lactose are still more preferred, and lactose is most preferred.

The amount of excipient included in the present invention as a function of total tablet weight may range from, for example, 30 to 90% by weight, with a range of 40 to 80% by weight preferable and a range of 45 to 75% by weight yet more preferable.

(e) Binder

Examples of binders that can be used in the present invention include water-soluble polymer binders commonly used in commercial preparations. Examples include methyl cellulose, hydroxypropyl cellulose, hydroxypropylmethyl cellulose, polyvinyl pyrrolidone, and polyvinyl alcohol-based resins. Methyl cellulose and polyvinyl alcohol-based resins are more preferable. Polyvinyl alcohol-based resins are yet more preferable. Preferred examples of polyvinyl alcohol-based resins include polyvinyl alcohol (PVA), polyvinyl alcohol derivatives, and polyvinyl alcohol copolymers. Polyvinyl alcohol is particularly preferred. Said binders can be used alone or in a combination of two or more. The amount of binder included in the present invention as a function of total tablet weight is selected in a range from, for example, 0.1 to 10% by weight, with a range of 0.2 to 5% by weight preferable, a range of 0.5 to 4% by weight more preferable and a range of 1 to 3% by weight particularly preferable.

As used herein, the terms "polyvinyl alcohol-based resin" and "polyvinyl alcohol" are synonymous with the terms defined in the section pertaining to the film base above.

The content of the "polyvinyl alcohol-based resin" used in the present invention, based on total tablet weight, may be, for example, 0.1 to 10% by weight, preferably 0.2 to 5% by weight, more preferably 0.5 to 4% by weight, and even more preferably 1 to 3% by weight.

(f) Disintegrant

Examples of disintegrants which can be used in the present invention include disintegrants commonly used in commercial preparations, such as starches, low-substituted hydroxypropyl cellulose, carmellose, calcium carmellose, sodium carmellose, crospovidone, sodium croscarmellose, and sodium carboxymethyl starch (also referred to as sodium starch glycolate). Preferable examples of disintegrants include starch, low-substituted hydroxypropyl cellulose, carmellose, crospovidone and sodium croscarmellose, with starch, low-substituted hydroxypropyl cellulose and crospovidone more preferable, and starch and crospovidone particularly preferable. Starches should more preferably correspond to pre-gelatinized starches, and partially pre-gelatinized starch is particularly preferred. These disintegrants can be used singly or in combinations of two or more.

When two or more disintegrants are combined, two disintegrants may be preferably combined, for example, preferably a combination of a starch and crospovidone or a combination of low-substituted hydroxypropyl cellulose and crospovidone, and more preferably a combination of partly pre-gelatinized starch and crospovidone.

The amount of disintegrant used in the present invention, based on total tablet weight, is, for example, from 5 to 50% by weight, with 5 to 40% by weight preferable, 10 to 40% by weight more preferable, 10 to 30% by weight yet more preferable and 10 to 25% by weight yet more preferable.

In another embodiment of the present invention, when two or more disintegrants are combined, and particularly when two disintegrants, for example, are combined, the content of one disintegrant (such as a starch, low-substituted hydroxypropyl cellulose, or partly pre-gelatinized starch), based on total tablet weight, is, for example, 5 to 50% by weight, preferably 5 to 40% by weight, more preferably 10 to 40% by weight, still more preferably 10 to 30% by weight, and even more preferably 15 to 25% by weight, and the content of the other disintegrant (such as crospovidone), based on total tablet weight, is, for example, 0.1 to 10% by weight, preferably 0.5 to 8% by weight, and more preferably 1 to 5% by weight.

(g) Lubricant

A lubricant may be added as a component of said tablet. Depending on the type of raw pharmaceutical ingredient or granules used, a lubricant is expected to prevent raw pharmaceutical ingredients or granules from adhering to punches during tableting, resulting in more efficient production of tablets. The types of lubricant used in the present invention include but are not limited to, for example, stearic acid, magnesium stearate, calcium stearate, sodium stearyl fumarate, talc, carnauba wax, and sucrose fatty acid esters. Stearic acid, magnesium stearate, calcium stearate, sodium stearyl fumarate, and sucrose fatty acid esters are preferred, magnesium stearate, calcium stearate, and sodium stearyl fumarate are more preferred, magnesium stearate and sodium stearyl fumarate are yet more preferred and magnesium stearate is particularly preferred. Said lubricants can be used alone or in a combination of two or more. The lubricant may be mixed with the other components prior to tableting, or may be sprayed onto the punch during tableting.

When an internal lubrication method is employed, the amount in which the lubricant is blended in the present invention, based on total tablet weight, is, for example, 0.2 to 3% by weight, preferably 0.3 to 2% by weight, and more preferably 0.5 to 1.5% by weight. When an external lubrication method is employed, the amount based on total tablet weight is, for example, 0.01 to 1.0% by weight, and preferably 0.05 to 0.5% by weight.

In addition to the above, the following additives may be added, provided that the function of the present invention is not thereby compromised. Examples include sweeteners, flavoring agents, odor enhancing agents, fragrance, fluidizers (such as Aerosil), antistatic agents, plasticizers, and antiagglomerants.

Although the present invention is not necessarily limited thereby, examples where FC tablets, for example, are prepared using, for example, a wet granulation method are given below.

(1) Preparation of Aqueous Binder Solution

The binding agent is dissolved in purified water. The amount of binder per amount of purified water is selected from a range of, for example, 1 to 20% by weight, with a range of 2 to 8% by weight preferred.

(2) Preparation of Granules Containing Obeticholic Acid

Granulation is carried out while the binder prepared in Step (1) above is dispersed in a fluid bed granulator containing obeticholic acid, a water-soluble excipient, and a disintegrant.

Examples of granulators include those designated for use in methods such as fluid bed granulation, high shear granulation, roto-fluid bed granulation, and double screw wet granulation. However, the invention is not limited to these.

When double screw wet granulation is used as a granulation method, the method for adding the binder may involve adding the binder in the form of a powder, in the form of a solution, or in the form of both a powder and solution.

(3) Drying of the Granulated Material:

The granulated material described above is dried at reduced or ordinary pressure. The material is dried so that loss on drying, as determined using an infrared aquameter, is no more than, for example, 3% by weight, or preferably no more than 1 to 2% by weight.

(4) Addition of Lubricant:

A lubricant is added to and mixed with the granulated material dried in (3) above. Mixing is performed using, for example, a mixer classified as a diffusion mixer (tumbler). Specific examples include tumble blenders, V blenders, double cones, and bin tumblers. However, the invention is not limited to these.

(5) Tableting:

The above mixture is tableted to prepare tablets. Examples of tableters include tableters classified as, for example, a tablet press. The degree of tableting hardness is selected from a range of, for example, 30 to 200 N.

(6) Application of Film Coating:

A film coating is applied to the tablets using a film coating agent as described above. Examples of coating devices include devices classified as coating pans. Devices classified as perforated coating systems are preferred.

(7) Drying:

The tablets obtained as described above are dried. Drying is carried out at reduced pressure or ordinary pressure, so that the level of loss on drying, as determined using an infrared aquameter, does not exceed, for example, 3% by weight, with 1 to 2% by weight preferred.

EXAMPLES

Examples, test examples, and comparative examples are given below to describe the present invention in further detail, but the present invention is not limited to said examples.

Unless otherwise specified, the following additives were used in the examples, test examples, and comparative examples.
Mannitol (Parritol 50C): Rocket Japan
Crystalline cellulose (Ceolus PH101): Asahi Kasei Chemicals
Corn starch (JP Matsutani cornstarch): Matsutani Kagaku
Lactose (Pharmatose 200M): DFE Pharma
Anhydrous lactose (Tablettose 80): MEGGLE
Partially pre-gelatinized starch (PCS PC-10): Asahi Kasei Chemicals
Crospovidone (Kollidon CL): BASF
Sodium carboxymethyl starch (Primojel): DMV
Carboxymethyl cellulose (NS-300): Nitiline
Low-substituted hydroxypropyl cellulose (L-HPC LH-31): Shin-Etsu Chemicals
Sodium croscarmellose (Ac-Di-Sol): FMC
Calcium hydrogen phosphate (Calcium Hydrogen Phosphate T): Tomita Pharmaceuticals
Anhydrous calcium hydrogen phosphate (Anhydrous Calcium Hydrogen Phosphate): Tomita Pharmaceuticals
Precipitated calcium carbonate (Precipitated Calcium Carbonate): Bihoku Funka Kogyo
Light anhydrous silicic acid (AEROSL 200): Nippon Aerosil
Hydroxypropylcellulose (HPC-SL): Nippon Soda
Methylcellulose (SM-4): Shin-Etsu Chemicals
Hydroxypropylmethyl cellulose (TC-5E): Shin-Etsu Chemicals
Polyvinyl alcohol (partially saponified product) (Gohsenol EG-05P): Nippon Synthetic Chemical Industry Co., Ltd.
Polyvinylpyrrolidone K30 (PVP K-30): BASF
Copovidone (Kollidon VA-64): BASF
Sodium lauryl sulfate (SLS): Nikko Chemicals
Triethyl citrate (Citroflex-2): Morimura Bros., Inc.
Triacetin (Triacetin): Daihachi Chemical Industry
Concentrated glycerin (Concentrated Glycerol-S): NOF
Propylene glycol (Propylene Glycol): ADEKA
Polysorbate 80 (Polysorbate 80 (RS)): NOF
Macrogol 400 (Polyethylene Glycol 400): NOF
Macrogol 6000 (Polyethylene Glycol 6000): NOF
Glyceryl monostearate (MGS-BMV): Nikko Chemicals
Sorbitan sesquioleate (S0-15V): Nikko Chemicals
Carnauba wax (Polishing Wax-105): Freund Corporation
Obeticholic acid (purchased from Intercept Pharmaceuticals Inc.) was used in free amorphous form.

The test methods used in these examples, test examples and comparative examples are as follows.

Comparative Example 1: Obeticholic Acid 10 mg FC Tablets

Patent Document 2 discloses tablets containing 1 to 25 mg of obeticholic acid. More specifically, said document discloses tablets that contain 1 to 25 mg of obeticholic acid, 157 to 185 mg of microcrystalline cellulose, 12 mg of sodium starch glycolate, 2 mg of magnesium stearate, 4 mg of colloidal silicon dioxide, and 8 mg of a coating material (per tablet). Table 1 shows the formulation of the FC tablets containing 10 mg obeticholic acid as described in Patent Document 2. Obeticholic acid 10 mg FC tablets used in Comparative Example 1 were prepared via dry granulation and for Opadry II® White, Macrogol 4000 (Polyethylene Glycol 4000) was included as a plasticizer component.

TABLE 1

Formulation of obeticholic acid FC tablets (Patent Document 2)

| Component | Comparative Example 1 Amount (mg) per tablet |
|---|---|
| Obeticholic acid | 10.0 |
| Microcrystalline cellulose | 176.0 |
| Sodium starch glycolate | 12.0 |
| Magnesium stearate | 2.0 |
| Opadry II ® White | 8.0 |
| Total | 208.0 |

<Storage>

The tablet containing 10 mg of obeticholic acid produced for Comparative Example 1 was stored under the following conditions. The amounts of obeticholic acid dimer generated before (initial) and after storage were measured in accordance with Test Example 1.

One month (1 M) and 3 months (3 M) at 40° C. and 75% RH under open conditions

Four weeks (4 W) at 50° C. and 85% RH (open)

Four weeks (4 W) at 60° C. under closed conditions

Test Example 1

<Preparation of Sample Solution>

One tablet containing 10 mg obeticholic acid (per tablet) that had been retrieved from storage was placed into a 20 mL graduated measuring flask. Acetonitrile/water (9/1) was added to the graduated measuring flask, the contents were ultrasounded (10 min) and it was confirmed that the tablet had disintegrated. The contents were thoroughly shaken (60 min at 300 rpm) using a shaker, and were again ultrasounded (10 min) to extract the obeticholic acid. Acetonitrile/water (9/1) was added to a constant volume, followed by centrifugation (10 min at 3000 rpm), and the supernatant was taken as a sample for HPLC assay (500 µg/mL obeticholic acid).

<Preparation of Standard Solution>

50 mg of obeticholic acid was weighed out into a 100 mL graduated measuring flask and dissolved in acetonitrile/water (9/1) (500 µg/mL). The resulting solution was diluted with acetonitrile/water (9/1) to prepare 15.0 µg/mL (3.0%), 5.0 µg/mL (1.0%), 0.25 µg/mL (0.05%) standard solutions.

<Quantification>

The aforementioned three standard solutions were used to produce a calibration curve, and the amount of obeticholic acid dimer contained in the sample solutions was quantified. The conditions pertaining to the analysis are shown below.

<Analysis Conditions>
Detector: Charged particle detector
Column: by Sigma-Aldrich, SIJPELCO Discovery C8 (particle size: 5 µm; internal
diameter: 4.6 mm; length: 15 cm)
Mobile phase: Acetonitrile/methanol/acetic acid aqueous solution (pH 3.0) mixture (8/1/1)
Analysis time: 15 min
Flow rate: 1.0 mL/min.
Column temperature: 30° C.
Injection volume: 100 µL
Sample cooler temperature: 10° C.
Syringe cleaning solution: Acetonitrile/methanol/acetic acid aqueous solution (pH 3.0) mixture (8/1/1)
Sample-dissolving solvent: Acetonitrile/water (9/1)
Charged Particle Detector Parameters
Gas: Nitrogen
Gas pressure: 35 psi
Range: 100 pA
Filter: High <Results>

Evaluation results pertaining to Comparative Example 1 are shown in Tables 2 and 3. Following storage under the aforementioned conditions, a marked increase in obeticholic acid dimerization was observed. In particular, following storage for 1 M and 3 M at 40° C. and 75% RH under open conditions, dimer generation exceeding 0.5% was observed.

TABLE 2

Amount of obeticholic acid dimer production (%)

|  | Initial | 40° C., 75% RH, open | | 50° C., 85% RH, open, 4 W | 60° C., closed, 4 W |
| --- | --- | --- | --- | --- | --- |
|  |  | 1 M | 3 M | | |
| Comparative Example 1 | 0.25 | 0.57 | 1.55 | 2.56 | 2.73 |

TABLE 3

Increase (%) in obeticholic acid dimerization from initial product

|  | 40° C., 75% RH, open | | 50° C., 85% RH, open, 4 W | 60° C., closed, 4 W |
| --- | --- | --- | --- | --- |
|  | 1 M | 3 M | | |
| Comparative Example 1 | 0.32 | 1.30 | 2.31 | 2.48 |

In order to investigate the cause of the increase in obeticholic acid dimerization, the effect of the film coating formulation on obeticholic acid dimerization was evaluated. Obeticholic acid (as an unmodified single-substance crude drug which did not include any additives whatsoever; a state which hereafter is referred to simply as "unmodified") was used as a basis for comparison.

Comparative Example 2: Obeticholic Acid 10 mg FC Tablets

A. Formulation of FC Tablets Containing 10 mg Obeticholic Acid

Uncoated tablets comprising the following composition and FC tablets were prepared, in that sequence.

(a) Uncoated Tablet Formulation and Incorporation Amount

TABLE 4

Uncoated tablet formulation and incorporation amount

| | Comparative Example 2 | |
| --- | --- | --- |
| Component | Amount per tablet (mg) | Incorporation amount (g) |
| Obeticholic acid | 10.0 | 50.0 |
| Lactose | 100.6 | 503.0 |
| Crospovidone | 7.0 | 35.0 |
| Low-substituted hydroxypropyl cellulose | 21.0 | 105.0 |
| Magnesium stearate (plant-derived) | 1.4 | 7.0 |
| Subtotal | 140.0 | 700.0 |

(b) FC Tablet Formulation

TABLE 5

FC tablet formulation

| | Comparative Example 2 |
| --- | --- |
| Component | Amount (mg) per tablet |
| Uncoated tablet | 140.0 |
| Polyvinyl alcohol | 1.6 |
| Talc | 0.6 |
| Titanium oxide | 1.0 |
| Polyethylene glycol 4000 | 0.8 |
| Total | 144.0 |

B. Manufacturing Method (1) Mixing:

Based on the incorporation amounts given in Table 4, 50 g of obeticholic acid, 503 g of lactose (Dilactose S: Freund), 35 g of crospovidone (Polyphenylene XL-10: BASF) and 105 g of low substituted hydroxypropyl cellulose (L-HPC LH-21: Shin-Etsu Chemical) were placed in a PE bag and thoroughly mixed by hand. 7.0 g of magnesium stearate (plant-derived: Taihei Chemical Industry Co., Ltd.) was added thereto and mixing was performed to obtain granules for tableting.

(2) Tableting:

The tableting granules prepared in (1) above were tableted under the following conditions using a rotary tablet press (VEL2, by Kikusui Seisakusho Ltd.) to obtain approximately 140 mg (per tablet) uncoated tablets.
Punch: Round-faced (R) tablet
Punch size: ϕ47 mm, 10 R
Disk speed: 20 rpm
Tableter compression pressure: Tablets were prepared to a tablet hardness of 60 to 140 N.

(3) Coating:

<Preparation of Coating Solution>

A coating solution with a solids concentration of 15% was prepared to form a coating layer having the composition shown in Table 5. Opadry® having the component composition shown in Table 5 and containing Macrogol 4000 (Polyethylene Glycol 4000) as a plasticizer was added to purified water where it was suspended and dispersed. Suspension 1 prepared thereby was sieved with a nylon mesh (150 #) to prepare a coating solution.

<Coating>

Uncoated tablets prepared in (2) above were coated under the following conditions such that the volume of the coating agent film was approximately 4 mg using a Ili-Coater IICT-30N (by Freund Corporation), to obtain FC tablets.

<FC Conditions>
Supplied air temperature: 85° C.
Air flow: 0.6 m³/min
Pan speed: 24 rpm
Spray pressure: 0.15 MPa
Solution rate: 3 to 5 g/min
Spraying distance: 11 cm A variety of suitable compositions (coating agents) for film coating are generally available, including products which are sold by Colorcon, Inc. under the trade names Opadry and Opadry II and it is also possible to purchase custom made formulations from the same company; these compositions may or may not contain appropriate amounts of the various film bases and plasticizers (e.g., polyethylene glycol, lecithin, glyceryl monostearate, propylene glycol, etc.) described above and can be conveniently used by suitably selecting them as a coating agent for use in the following examples.

Example 1

Uncoated tablets obtained in Comparative Example 2 were used to obtain film-coated tablets in the same manner described in Comparative Example 2 with the exception that the aforementioned commercially available coating agent containing lecithin as a plasticizer was used.

Example 2

Uncoated tablets obtained in Comparative Example 2 were used to obtain film-coated tablets in the same manner described in Comparative Example 2 with the exception that the aforementioned commercially available coating agent containing glyceryl monostearate as a plasticizer was used.

Example 3

Uncoated tablets obtained in Comparative Example 2 were used to obtain film-coated tablets in the same manner described in Comparative Example 2 with the exception that the aforementioned commercially available coating agent not containing a plasticizer was used and the solids concentration of the coating solution was adjusted to 10%.

Example 4

Uncoated tablets obtained in Comparative Example 2 were used to obtain film-coated tablets in the same manner described in Comparative Example 2 with the exception that the aforementioned commercially available coating agent containing propylene glycol as a plasticizer was used and the solids concentration of the coating solution was adjusted to 10%.

Example 5

FC tablets were obtained in the same manner as in Comparative Example 2, except for the change in the FC component.

<Preparation of Coating Solution>

A coating solution with a solids concentration of 10% was prepared to form a coating layer for each tablet having the composition shown in Table 6. Hydroxypropylmethylcellulose (TC-5R: Nippon Soda) as well as the plasticizer triethyl citrate (Citroflex-2: Morimura Shoji) were added to purified water and dissolved (Solution 1). Separately, talc (Talcan Hayashi: Hayashi Kasei) and titanium oxide (Titanium Oxide NA 61: Toho Titanium) were added to purified water where they were suspended and dispersed (Suspension 1). Solution 1 was added to and dispersed in suspension 1, and the solution was sifted using a sieve (150 #) to prepare a coating solution.

TABLE 6

| FC tablet formulation | |
| --- | --- |
| Component | Example 5 Amount (mg) per tablet |
| Uncoated tablet | 140.0 |
| Hydroxypropylmethyl cellulose | 3.00 |
| Talc | 0.35 |
| Titanium oxide | 0.50 |
| Triethyl citrate | 0.15 |
| Total | 144.0 |

The formulations of the obeticholic acid FC tablets prepared in Comparative Example 2 as well as Examples 1 to 5 are shown in Table 7.

TABLE 7

| Formulation of obeticholic acid FC tablets (mg) | | | | |
| --- | --- | --- | --- | --- |
| | Component | Comparative Example 2 | Example 1 | Example 2 |
| Uncoated tablet portion | Obeticholic acid | 10.0 | 10.0 | 10.0 |
| | Lactose | 100.6 | 100.6 | 100.6 |
| | Crospovidone | 7.0 | 7.0 | 7.0 |
| | Low-substituted hydroxypropyl cellulose | 21.0 | 21.0 | 21.0 |
| | Magnesium stearate (plant-derived) | 1.4 | 1.4 | 1.4 |
| FC portion | Polyvinyl alcohol | 1.60 | — | — |
| | Talc | 0.59 | — | — |
| | Titanium oxide | 1.00 | — | — |
| | Polyethylene glycol 4000 (plasticizer) | 0.81 | — | — |
| | Coating agent containing lecithin as a plasticizer | — | 4.00 | — |
| | Coating agent containing glyceryl monostearate as a plasticizer | — | — | 4.00 |

TABLE 7-continued

Formulation of obeticholic acid FC tablets (mg)

|  |  |  |  |  |
|---|---|---|---|---|
|  | Coating agent not containing plasticizer | — | — | — |
|  | Coating agent containing propylene glycol as a plasticizer | — | — | — |
|  | Hydroxypropylmethyl cellulose | — | — | — |
|  | Talc | — | — | — |
|  | Titanium oxide | — | — | — |
|  | Triethyl citrate (plasticizer) | — | — | — |
| Total |  | 144.0 | 144.0 | 144.0 |

|  | Component | Example 3 | Example 4 | Example 5 |
|---|---|---|---|---|
| Uncoated tablet portion | Obeticholic acid | 10.0 | 10.0 | 10.0 |
|  | Lactose | 100.6 | 100.6 | 100.6 |
|  | Crospovidone | 7.0 | 7.0 | 7.0 |
|  | Low-substituted hydroxypropyl cellulose | 21.0 | 21.0 | 21.0 |
|  | Magnesium stearate (plant-derived) | 1.4 | 1.4 | 1.4 |
| FC portion | Polyvinyl alcohol | — | — | — |
|  | Talc | — | — | — |
|  | Titanium oxide | — | — | — |
|  | Polyethylene glycol 4000 (plasticizer) | — | — | — |
|  | Coating agent containing lecithin as a plasticizer | — | — | — |
|  | Coating agent containing glyceryl monostearate as a plasticizer | — | — | — |
|  | Coating agent not containing plasticizer | 4.00 | — | — |
|  | Coating agent containing propylene glycol as a plasticizer | — | 4.00 | — |
|  | Hydroxypropylmethyl cellulose | — | — | 3.00 |
|  | Talc | — | — | 0.35 |
|  | Titanium oxide | — | — | 0.50 |
|  | Triethyl citrate (plasticizer) | — | — | 0.15 |
| Total |  | 144.0 | 144.0 | 144.0 |

<Storage>

The tablets containing 10 mg of obeticholic acid produced for Comparative Example 2 as well as Examples 1 to 5 were stored under the following conditions. The amounts of obeticholic acid dimer generated before (initial) and after storage were measured in accordance with Test Example 1.

One month (1 M) and 3 months (3 M) at 40° C. and 75% RH (open)

Four weeks (4 W) at 50° C. and 85% RH (open)

Four weeks (4 W) at 60° C. (closed)

Comparative Example 3: Obeticholic Acid (Unmodified) Stability

Obeticholic acid (unmodified) was weighed out in amounts of 5 mg into test tubes to serve as individual samples.

<Storage>

Test Lubes containing the obeticholic acid (unmodified) prepared in Example 1 were stored under the following conditions. The amounts of obeticholic acid dimer generated before (initial) and after storage were measured in accordance with Test Example 2.

Four weeks (4 W) at 50° C. and 85% RH (open)

Four weeks (4 W) at 60° C. (closed)

Test Example 2

The amount of obeticholic acid dimer generated was measured in the same manner described in Test Example 1, with the exception that the sample solution was prepared as follows.

<Preparation of Sample Solution>

Acetonitrile/water (9/1) was added in an amount of exactly 10 mL to test tubes that had been retrieved from storage, and the contents were ultrasounded to extract the obeticholic acid. Following centrifugation (10 min at 3000 rpm), the supernatant was made into samples for HPLC assay (500 µg/mL obeticholic acid).

<Results>

Evaluation results pertaining to Comparative Examples 1 to 3 as well as Examples 1 to 5 are shown in Tables 8 and 9. In Comparative Examples 1 and 2, wherein polyethylene glycol, which is generally used as a plasticizer, was used, proliferation of obeticholic acid dimers was markedly increased. In Example 3, wherein no plasticizer was used and in Examples 1, 2, 4, and 5 wherein lecithin, glyceryl monostearate, propylene glycol, and triethyl citrate were used as specific plasticizers, during storage of the film-coated tablets, proliferation of obeticholic acid dimers was significantly reduced compared to Comparative Examples 1 and 2 and proliferation was inhibited to the same extent as obeticholic acid (unmodified) (Comparative Example 3). In particular, that for the FC tablets obtained in Examples 1 to 5, dimer production was limited to less than 0.5% following storage for 1 M to 3 M at 40° C. and 75% RH (open) represents an excellent result.

TABLE 8

Amount of obeticholic acid dimer production (%)

| | Plasticizer used | | 40° C., 75% RH, open | | | 50° C., 85% RH, open, 4 W | 60° C., closed, 4 W |
|---|---|---|---|---|---|---|---|
| | | Initial | 1 M | 2 M | 3 M | | |
| Comparative Example 1 | Polyethylene glycol | 0.25 | 0.57 | — | 1.55 | 2.56 | 2.73 |
| Comparative Example 2 | Polyethylene glycol | 0.11 | 0.44 | 0.87 | 1.12 | 1.28 | 2.59 |
| Comparative Example 3 | None (unmodified obeticholic acid) | 0.04 | — | — | — | 0.83 | 0.81 |
| Example 1 | Lecithin | 0.10 | 0.18 | 0.35 | 0.42 | 0.66 | 0.81 |
| Example 2 | Glyceryl monostearate | 0.11 | 0.19 | 0.35 | 0.41 | 0.68 | 0.78 |
| Example 3 | None | 0.10 | 0.19 | 0.35 | 0.40 | 0.62 | 0.85 |
| Example 4 | Propylene glycol | 0.11 | 0.20 | 0.32 | 0.40 | 0.60 | 0.82 |
| Example 5 | Triethyl citrate | 0.12 | 0.19 | 0.33 | 0.41 | 0.58 | 0.78 |

TABLE 9

Increase (%) in obeticholic acid dimerization from initial product

| | Plasticizer used | 40° C., 75% RH, open | | | 50° C., 85% RH, open, 4 W | 60° C., closed, 4 W |
|---|---|---|---|---|---|---|
| | | 1 M | 2 M | 3 M | | |
| Comparative Example 1 | Polyethylene glycol | 0.32 | — | 1.30 | 2.31 | 2.48 |
| Comparative Example 2 | Polyethylene glycol | 0.33 | 0.76 | 1.01 | 1.17 | 2.48 |
| Comparative Example 3 | None (unmodified obeticholic acid) | — | — | — | 0.79 | 0.77 |
| Example 1 | Lecithin | 0.08 | 0.25 | 0.32 | 0.56 | 0.71 |
| Example 2 | Glyceryl monostearate | 0.08 | 0.24 | 0.30 | 0.57 | 0.67 |
| Example 3 | None | 0.09 | 0.25 | 0.30 | 0.52 | 0.75 |
| Example 4 | Propylene glycol | 0.09 | 0.21 | 0.29 | 0.49 | 0.71 |
| Example 5 | Triethyl citrate | 0.07 | 0.21 | 0.29 | 0.46 | 0.66 |

The effect of the uncoated tablet formulation on obeticholic acid dimerization was evaluated.

Example 6-(1): Obeticholic Acid 20 mg FC Tablets

A. Formulation of FC Tablets Containing 20 mg Obeticholic Acid

Granules comprising the following composition, uncoated tablets, and FC tablets were prepared, in that sequence.

(a) Granule Formulation and Incorporation Amount

TABLE 10

Granule formulation and incorporation amount

| | Example 6-(1) | |
|---|---|---|
| Component | Amount per tablet (mg) | Incorporation amount (g) |
| Obeticholic acid | 20.0 | 128.57 |
| Lactose | 83.6 | 537.43 |

TABLE 10-continued

Granule formulation and incorporation amount

| | Example 6-(1) | |
|---|---|---|
| Component | Amount per tablet (mg) | Incorporation amount (g) |
| Partially pre-gelatinized starch | 28.0 | 180.00 |
| Crospovidone | 4.2 | 27.00 |
| Polyvinyl alcohol (partially saponified product) | 2.8 | 18.00 |
| Subtotal | 138.6 | 891.0 |

(b) Uncoated Tablet Formulation and Incorporation Amount

TABLE 11

Uncoated tablet formulation and incorporation amount

| | Example 6-(1) | |
|---|---|---|
| Component | Amount per tablet (mg) | Incorporation amount (g) |
| Granules | 138.6 | 792.00 |
| Magnesium stearate (plant-derived) | 1.4 | 8.00 |
| Subtotal | 140.0 | 800.0 |

(c) FC Tablet Formulation

TABLE 12

FC tablet formulation

| Component | Example 6-(1) Amount (mg) per tablet |
|---|---|
| Uncoated tablet | 140.0 |
| Hydroxypropylmethyl cellulose | 3.00 |
| Talc | 0.61 |
| Titanium oxide | 0.24 |
| Triethyl citrate (plasticizer) | 0.15 |
| Carnauba wax | Trace amount |
| Total | 144.0 |

B. Manufacturing Method
(1) Granulation and Sizing
<Preparation of Binder Solution>
Polyvinyl alcohol serving as a water-soluble polymer binder was added to and dissolved in purified water that had been heated to 80° C. The mixture was allowed to cool to room temperature, and purified water was added to prepare a 4% binder solution.
<Granulation>
A non-polyvinyl alcohol formulation was incorporated into a fluid bed granulator (Multiplex MP-01, by Powrex Corporation) in accordance with the incorporation amounts given in Table 10, and spray granulation was carried out under the following conditions using the binder solution prepared in (1) above to obtain granules.
<Granulation Conditions>
Supplied air temperature: 75° C.
Air flow: 30 to 50 m$^3$/hr
Spray rate: 8 to 12 g/min
Spray nozzle diameter: 1.0 mm
Spray pressure: 0.1 MPa
Spray gun position: Intermediate level
<Sizing>
The resulting granules were sifted using a mesh having a screen size of 710 µm to obtain sized granules.
(2) Mixing of Granules and Lubricant:
Magnesium stearate was added to the granules prepared in (1) above in the incorporation amount noted in Table 11, and the material was mixed (40 rpm, 5 min) using a small V mixer (Tsutsui Scientific Instruments Co., Ltd.) to obtain tableting granules.
(3) Tableting:
The tableting granules prepared in (2) above were tableted under the following conditions using a rotary tablet press (VEL2, by Kikusui Seisakusho Ltd.) to obtain approximately 140 mg (per tablet) uncoated tablets.
Punch: Round-faced (R) tablet
Punch size: 07 mm, 10 R
Disk speed: 20 rpm
Tableter compression pressure: Tablets were prepared to a tablet hardness of 60 to 140 N.
(4) Coating:
<Preparation of Coating Solution>
A coating solution with a solids concentration of 10% was prepared to form a coating layer having the composition shown in Table 12. Hydroxypropylmethyl cellulose and triethyl citrate were added to and dissolved in purified water (solution 1). Separately, talc and titanium oxide were added to and suspended/dispersed in purified water (Suspension 1). Solution 1 was added to and dispersed in Suspension 1, and the solution was sifted using nylon mesh (150 #) to prepare a coating solution.
<Coating>
Uncoated tablets prepared in (3) above were coated under the following conditions such that the volume of the coating agent film was approximately 4 mg using a Hi-Coater HCT-30N (by Freund Corporation), to obtain FC tablets. Carnauba wax was added after the drying step in the film coating process.
<Fc Conditions>
Supplied air temperature: 85° C.
Air flow: 0.6 m$^3$/min
Pan speed: 24 rpm
Spray pressure: 0.15 MPa
Solution rate: 3 to 5 g/min
Spraying distance: 11 cm Example 6-(2): Obeticholic Acid 20 mg FC Tablets FC tablets were obtained in the same manner as in Example 6-(1), with the exception that the partly pre-gelatinized starch content per tablet was 21 mg, and lactose was used to adjust for the difference in the composition.

Example 6-(3): Obeticholic Acid 20 mg FC Tablets

FC tablets were obtained in the same manner as in Example 6-(1), with the exception that the FC composition was altered.
<Preparation of Coating Solution>
A coating solution with a solids concentration of 15% was prepared to form a coating layer having the composition shown in Table 13. Polyvinyl alcohol and triethyl acetate were added to and dissolved in purified water (solution 1). Separately, talc and titanium oxide were added to and suspended/dispersed in purified water (Suspension 1). Solution 1 was added to and dispersed in Suspension 1, and the solution was sifted using nylon mesh (150 #) to prepare a coating solution.

Example 6-(4): Obeticholic Acid 20 mg FC Tablets

FC tablets were obtained in the same manner as in Example 6-(1), with the exception that the partly pre-gelatinized starch content per tablet was 35 mg, and lactose was used to adjust for the difference in the composition.

Example 6-(5): Obeticholic Acid 20 mg FC Tablets

FC tablets were obtained in the same manner as in Example 6-(1), except that the formulation did not contain crospovidone, and lactose was used to adjust for the difference in the composition.

Example 6-(6): Obeticholic Acid 20 mg FC Tablets

FC tablets were obtained in the same manner as in Example 6-(1), with the exception that the polyvinyl alcohol content per tablet was adjusted to 1.4 mg, and lactose was used to adjust for the difference in the composition.

Example 6-(7): Obeticholic Acid 20 mg FC Tablets

FC tablets were obtained in the same manner as in Example 6-(1), with the exception that the polyvinyl alcohol content per tablet was adjusted to 4.2 mg, and lactose was used to adjust for the difference in the composition.

Example 6-(8): Obeticholic Acid 20 mg FC Tablets

FC tablets were obtained in the same manner as in Example 6-(1), with the exception that the magnesium stearate content per tablet was adjusted to 0.7 mg, and lactose was used to adjust for the difference in the composition.

Example 6-(9): Obeticholic Acid 20 mg FC Tablets 2.1 mg of magnesium stearate was mixed into the granules prepared in Example 6-(8) to prepare a uncoated tablet of approximately 141.4 mg. FC tablets were then obtained in the same manner as in Example 6-(8).

Example 6-(10): Obeticholic Acid 2.5 mg FC Tablets

FC tablets were obtained in the same manner as in Example 6-(1), with the exception that the obeticholic acid content per tablet was adjusted to 2.5 mg, and lactose was used to adjust for the difference in the composition.

Example 6-(11): Obeticholic Acid 20 mg FC Tablets

FC tablets were obtained in the same manner as in Example 6-(1), with the exception that low-substituted hydroxypropyl cellulose was used in lieu of partly pre-gelatinized starch and the amount per tablet was 16.8 mg, and lactose was used to adjust for the difference in the composition.

Table 13 shows the formulations of the obeticholic acid FC tablets obtained in Examples 6-(1) to 6-(11).

TABLE 13

Formulation of obeticholic acid FC tablets (mg)

| | Component | Example 6-(1) | Example 6-(2) | Example 6-(3) | Example 6-(4) |
|---|---|---|---|---|---|
| Uncoated tablet portion | Obeticholic acid | 20.0 | 20.0 | 20.0 | 20.0 |
| | Lactose | 83.6 | 90.6 | 90.6 | 76.6 |
| | Partially pre-gelatinized starch | 28.0 | 21.0 | 21.0 | 35.0 |
| | Low-substituted hydroxypropyl cellulose | — | — | — | — |
| | Crospovidone | 4.2 | 4.2 | 4.2 | 4.2 |
| | Polyvinyl alcohol (partially saponified product) | 2.8 | 2.8 | 2.8 | 2.8 |
| | Magnesium stearate (plant-derived) | 1.4 | 1.4 | 1.4 | 1.4 |
| FC portion | Hydroxypropylmethyl cellulose | 3.00 | 3.00 | — | 3.00 |
| | Polyvinyl alcohol (partially saponified product) | — | — | 1.60 | — |
| | Talc | 0.61 | 0.61 | 1.93 | 0.61 |
| | Titanium oxide | 0.24 | 0.24 | 0.32 | 0.24 |
| | Triethyl citrate (plasticizer) | 0.15 | 0.15 | 0.15 | 0.15 |
| | Carnauba wax | Trace amount | Trace amount | Trace amount | Trace amount |
| Total | | 144.0 | 144.0 | 144.0 | 144.0 |

| | Component | Example 6-(5) | Example 6-(6) | Example 6-(7) | Example 6-(8) |
|---|---|---|---|---|---|
| Uncoated tablet portion | Obeticholic acid | 20.0 | 20.0 | 20.0 | 20.0 |
| | Lactose | 87.8 | 85.0 | 82.2 | 84.3 |
| | Partially pre-gelatinized starch | 28.0 | 28.0 | 28.0 | 28.0 |
| | Low-substituted hydroxypropyl cellulose | — | — | — | — |
| | Crospovidone | — | 4.2 | 4.2 | 4.2 |
| | Polyvinyl alcohol (partially saponified product) | 2.8 | 1.4 | 4.2 | 2.8 |
| | Magnesium stearate (plant-derived) | 1.4 | 1.4 | 1.4 | 0.7 |
| FC portion | Hydroxypropylmethyl cellulose | 3.00 | 3.00 | 3.00 | 3.00 |
| | Polyvinyl alcohol (partially saponified product) | — | — | — | — |
| | Talc | 0.61 | 0.61 | 0.61 | 0.61 |
| | Titanium oxide | 0.24 | 0.24 | 0.24 | 0.24 |
| | Triethyl citrate (plasticizer) | 0.15 | 0.15 | 0.15 | 0.15 |
| | Carnauba wax | Trace amount | Trace amount | Trace amount | Trace amount |
| Total | | 144.0 | 144.0 | 144.0 | 144.0 |

| | Component | Example 6-(9) | Example 6-(10) | Example 6-(11) |
|---|---|---|---|---|
| Uncoated tablet portion | Obeticholic acid | 20.0 | 2.5 | 20.0 |
| | Lactose | 84.3 | 101.1 | 94.8 |
| | Partially pre-gelatinized starch | 28.0 | 28.0 | — |

TABLE 13-continued

| | Formulation of obeticholic acid FC tablets (mg) | | | |
|---|---|---|---|---|
| | Low-substituted hydroxypropyl cellulose | — | — | 16.8 |
| | Crospovidone | 4.2 | 4.2 | 4.2 |
| | Polyvinyl alcohol (partially saponified product) | 2.8 | 2.8 | 2.8 |
| | Magnesium stearate (plant-derived) | 2.1 | 1.4 | 1.4 |
| FC portion | Hydroxypropylmethyl cellulose | 3.00 | 3.00 | 3.00 |
| | Polyvinyl alcohol (partially saponified product) | — | — | — |
| | Talc | 0.61 | 0.61 | 0.61 |
| | Titanium oxide | 0.24 | 0.24 | 0.24 |
| | Triethyl citrate (plasticizer) | 0.15 | 0.15 | 0.15 |
| | Carnauba wax | Trace amount | Trace amount | Trace amount |
| Total | | 145.4 | 144.0 | 144.0 |

<Storage>

Tablets containing 2.5 mg or 20 mg of obeticholic acid produced in Examples 6-(1) to 6-(11) were stored under the following conditions. The amounts of obeticholic acid dimer generated before (initial) and after storage were measured in accordance with the methods of Test Examples 3 and 4 given below.

One month (1 M) and 3 months (3 M) at 40° C. and 75% RH (open)
Four weeks (4 W) at 50° C. and 85% RH (open)
Four weeks (4 W) at 60° C. (closed)

Test Example 3: Evaluation of Obeticholic Acid 2.5 mg FC Tablets

The amount of obeticholic acid dimer generated was measured in the same manner described in Test Example 1, with the exception that the sample solution was prepared as follows.

<Preparation of Sample Solution>

Four tablets containing 2.5 mg obeticholic acid (per tablet) that had been retrieved from storage were introduced into a 20 mL graduated measuring flask. Acetonitrile/water (9/1) was added to the graduated measuring flask, the contents were ultrasounded (10 min) and it was confirmed that the tablet had disintegrated. The contents were thoroughly shaken (60 min at 300 rpm) using a shaker, and were again ultrasounded (10 min) to extract the obeticholic acid. Acetonitrile/water (9/1) was added to a constant volume, followed by centrifugation (10 min at 3000 rpm), and the supernatant was taken as a sample for HPLC assay (500 µg/mL obeticholic acid).

Test Example 4: Evaluation of Obeticholic Acid 20 mg FC Tablets

The amount of obeticholic acid dimer generated was measured in the same manner described in Test Example 1, with the exception that the sample solution was prepared as follows.

<Preparation of Sample Solution>

One tablet containing 20 mg obeticholic acid (per tablet) that had been retrieved from storage was introduced into a 40 mL graduated measuring flask. Acetonitrile/water (9/1) was added to the graduated measuring flask, the contents were ultrasounded (10 min) and it was confirmed that the tablet had disintegrated. The contents were thoroughly shaken (60 min at 300 rpm) using a shaker, and were again ultrasounded (10 min) to extract the obeticholic acid. Acetonitrile/water (9/1) was added to a constant volume, followed by centrifugation (10 min at 3000 rpm), and the supernatant was taken as a sample for HPLC assay (500 µg/mL obeticholic acid).

<Results>

Evaluation results pertaining to Examples 6-(1) to 6-(11) are shown in Tables 14 and 15.

For comparison, the results of Comparative Example 1 are also shown. As is clear from the results, for film-coated tablets which used triethyl citrate which is preferred as the specific plasticizer, the formulation of the uncoated tablet did not affect proliferation of obeticholic acid dimers, and proliferation of obeticholic acid dimers in Examples 6-(1) to 6-(11) was significantly reduced compared to Comparative Example 1, wherein polyethylene glycol was used as a plasticizer. In particular, for the FC tablets obtained in Example 6, represented by Examples 6-(1), 6-(7), 6-(10) and 6-(11), the fact that dimer production was limited to less than 0.5% following storage for 1 M and/or 3 M at 40° C. and 75% RH (open) represents an excellent result.

TABLE 14

| Amount of obeticiolic acid dimer production (%) | | | | | |
|---|---|---|---|---|---|
| | | 40° C., 75% RH, open | | 50° C., 85% RH, open, 4 W | 60° C., closed, 4 W |
| Example Number | Initial | 1 M | 3 M | | |
| Comparative Example 1 | 0.25 | 0.57 | 1.55 | 2.56 | 2.73 |
| Example 6-(1) | 0.08 | 0.20 | 0.37 | 0.71 | 0.78 |
| Example 6-(2) | 0.09 | — | — | 0.71 | 0.77 |
| Example 6-(3) | 0.08 | — | — | 0.73 | 0.88 |
| Example 6-(4) | 0.09 | — | — | 0.69 | 0.76 |
| Example 6-(5) | 0.08 | — | — | 0.78 | 0.80 |
| Example 6-(6) | 0.08 | — | — | 0.71 | 0.78 |
| Example 6-(7) | 0.08 | 0.20 | 0.38 | 0.74 | 0.78 |
| Example 6-(8) | 0.08 | — | — | 0.69 | 0.77 |
| Example 6-(9) | 0.07 | — | — | 0.70 | 0.86 |
| Example 6-(10) | 0.08 | 0.18 | 0.32 | 0.34 | 0.76 |
| Example 6-(11) | 0.08 | — | 0.37 | 0.68 | 0.81 |

TABLE 15

| Example Number | Increase (%) in obeticholic acid dimerization from initial product | | | |
|---|---|---|---|---|
| | 40° C., 75% RH, open | | 50° C., 85% RH, open, 4 W | 60° C., closed, 4 W |
| | 1 M | 3 M | | |
| Comparative Example 1 | 0.32 | 1.30 | 2.31 | 2.48 |
| Example 6-(1) | 0.12 | 0.29 | 0.63 | 0.70 |
| Example 6-(2) | — | — | 0.62 | 0.68 |
| Example 6-(3) | — | — | 0.65 | 0.80 |
| Example 6-(4) | — | — | 0.60 | 0.67 |
| Example 6-(5) | — | — | 0.70 | 0.72 |
| Example 6-(6) | — | — | 0.63 | 0.70 |
| Example 6-(7) | 0.12 | 0.30 | 0.66 | 0.70 |
| Example 6-(8) | — | — | 0.61 | 0.69 |
| Example 6-(9) | — | — | 0.63 | 0.79 |
| Example 6-(10) | 0.10 | 0.24 | 0.26 | 0.68 |
| Example 6-(11) | — | 0.29 | 0.60 | 0.73 |

Example 7: Obeticholic Acid 10 mg FC Tablets

A. Formulation of Film-Coated (FC) Tablets Containing 10 mg Obeticholic Acid

Granules comprising the following composition, uncoated tablets, and FC tablets were prepared, in that sequence.

(a) Granule Formulation and Incorporation Amount

TABLE 16

| | Granule formulation and incorporation amount | |
|---|---|---|
| | Example 7 | |
| Component | Amount per tablet (mg) | Incorporation amount (kg) |
| Obeticholic acid | 10.0 | 2.00 |
| Lactose | 93.6 | 18.72 |
| Partially pre-gelatinized starch | 28.0 | 5.60 |
| Crospovidone | 4.2 | 0.84 |
| Polyvinyl alcohol (partially saponified product) | 2.8 | 0.56 |
| Subtotal | 138.6 | 27.72 |

(b) Uncoated Tablet Formulation and Incorporation Amount

TABLE 17

| | Uncoated tablet formulation and incorporation amount | |
|---|---|---|
| | Example 7 | |
| Component | Amount per tablet (mg) | Incorporation amount (kg) |
| Granules | 138.6 | 25.55 |
| Magnesium stearate (plant-derived) | 1.4 | 0.26 |
| Subtotal | 140.0 | 25.80 |

(c) FC Tablet Formulation

TABLE 18

| | FC tablet formulation |
|---|---|
| Component | Example 7 Amount per tablet (mg) |
| Uncoated tablet | 140.0 |
| Hydroxypropylmethyl cellulose | 3.00 |
| Titanium oxide | 0.60 |
| Triacetin (plasticizer) | 0.40 |
| Carnauba wax | Trace amount |
| Total | 144.0 |

B. Manufacturing Method (1) Granulation and Sizing

<Preparation of Binder Solution>

Polyvinyl alcohol serving as a water-soluble polymer binder was added to and dissolved in purified water that had been heated to 80° C. The mixture was allowed to cool to room temperature, and purified water was added to prepare a 4% binder solution.

<Granulation>

A non-polyvinyl alcohol formulation was incorporated into a fluid bed granulator (flow coater, Model NFLIF-30SJC, Freund Corporation) in accordance with the incorporation amounts given in Table 16, and spray granulation was carried out under the following conditions using the binder solution prepared in (1) above to obtain granules.

<Granulation Conditions>

Supplied air temperature: 75° C.
Air flow: 6 to 8 m$^3$/min
Spray rate: 160 g/min
Spray nozzle diameter: 1.8 mm
Spray air pressure: 0.46 MPa <Sizing>

The resulting granules were sifted using a sanitary vibrating sieve (Model 502SB, Dalton Corporation) to obtain sized granules. A 710 g m screen size was used.

(2) Mixing of Granules and Lubricant:

Magnesium stearate was added to the sized granules prepared in (1) above in the incorporation amount noted in Table 17, and the material was mixed (20 rpm, 5 min) using a volume mixer (110 L, Yamakin (Japan) Co., Ltd.) to obtain tableting granules.

(3) Tableting:

The tableting granules prepared in (2) above were tableted under the following conditions using a rotary tablet press (AQU 30518SW2AII, by Kikusui Seisakusho Ltd.) to obtain approximately 140 mg uncoated tablets (per tablet).

Punch: Round-faced (R) tablet
Punch size: 07 mm, 10 R
Disk speed: 50 rpm
Tableter compression pressure: Tablets were prepared to a tablet hardness of 40 to 120 N.

(4) Coating:

<Preparation of Coating Solution>

A coating solution with a solids concentration of 10% was prepared to form a coating layer having the composition show in Table 18. Hydroxypropylmethyl cellulose and triacetin were added to and dissolved in purified water (Solution 1). Separately, titanium oxide was added to and suspended/dispersed in purified water (Suspension 1). Solution 1 was added to and dispersed in Suspension 1, and the solution was sifted using nylon mesh (150 #) to prepare a coating solution.

<Coating>

Uncoated tablets prepared in (3) above were coated under the following conditions such that the volume of the coating agent film was approximately 4 mg using a Hi-Coater HCT-30N (by Freund Corporation), to obtain FC tablets. Carnauba wax was added after the drying step in the film coating process.

<Fc Conditions>

Supplied air temperature: 85° C.
Air flow: 0.6 m³/min
Pan speed: 24 rpm
Spray pressure: 0.15 MPa
Solution rate: 3 to 5 g/min
Spraying distance: 11 cm Example 8: Obeticholic Acid 10 mg FC Tablets Film coating of the uncoated tablets prepared in Example 7 was performed to obtain FC tablets. FC tablets were obtained in the same manner described in Example 7 with the exception that polyoxyethylene sorbitan monooleate (Polysorbate 80) was used in lieu of triacetin.

Table 19 shows the formulations of the obeticholic acid FC tablets obtained in Examples 7 and 8.

TABLE 19

Formulation of obeticholic acid FC tablets (mg)

| | Component | Example 7 | Example 8 |
|---|---|---|---|
| Uncoated tablet portion | Obeticholic acid | 10.0 | 10.0 |
| | Lactose | 93.6 | 93.6 |
| | Partially pre-gelatinized starch | 28.0 | 28.0 |
| | Crospovidone | 4.2 | 4.2 |
| | Polyvinyl alcohol (partially saponified product) | 2.8 | 2.8 |
| | Magnesium stearate (plant-derived) | 1.4 | 1.4 |
| FC portion | Hydroxypropyl methyl cellulose | 3.00 | 3.00 |
| | Titanium oxide | 0.60 | 0.60 |
| | Triacetin (plasticizer) | 0.40 | — |
| | Polyoxyethylene sorbitan monooleate (plasticizer) | — | 0.40 |
| | Carnauba wax | Trace amount | Trace amount |
| Total | | 144.0 | 144.0 |

<Storage>

The tablets containing 10 mg of obeticholic acid produced for Examples 7 and 8 were stored under the following conditions. The amounts of obeticholic acid dimer generated before (initial) and after storage were measured in accordance with the methods of Test Example 1.

Four weeks (4 W) at 50° C. and 85% RH (open)
Four weeks (4 W) at 60° C. (closed)

<Results>

Evaluation results pertaining to Examples 7 and 8 are shown in Tables 20 and 21.

For comparison, the results of Comparative Example 1 are also shown. The increase in obeticholic acid dimerization observed during storage of film-coated tablets which used triacetin or polyoxyethylene sorbitan monooleate (Polysorbate 80) which are preferred as the specific plasticizer was significantly lower compared to Comparative Example 1, wherein polyethylene glycol was used as a plasticizer.

TABLE 20

Amount of obeticholic acid dimer production (%)

| | Plasticizer used | Initial | 50° C., 85% RH, open, 4 W | 60° C., closed, 4 W |
|---|---|---|---|---|
| Comparative Example 1 | Polyethylene glycol | 0.25 | 2.56 | 2.73 |
| Example 7 | Triacetin | 0.19 | 0.80 | 0.94 |
| Example 8 | Polyoxyethylene sorbitan monooleate | 0.19 | 0.73 | 0.88 |

TABLE 21

Increase (%) in obeticholic acid dimerization from initial product

| | Plasticizer used | 50° C., 85% RH, open, 4 W | 60° C., closed, 4 W |
|---|---|---|---|
| Comparative Example 1 | Polyethylene glycol | 2.31 | 2.48 |
| Example 7 | Triacetin | 0.61 | 0.75 |
| Example 8 | Polyoxyethylene sorbitan monooleate | 0.55 | 0.69 |

Example 9: Obeticholic Acid 20 mg FC Tablets (Double Screw Wet Granulation Method)

Obeticholic acid 285. 7 g, lactose hydrate 1354. 29 g, low-substituted hydroxypropyl cellulose 240.0 g, and crospovidone 60.0 g were weighed out and mixed in a plastic bag. The powder mixture was introduced into the powder supply feeder of a double screw wet granulator. The powder mixture was fed at a rate of 20 kg/hour from the powder supply feeder into the chamber, and as 8.5% per weight polyvinyl alcohol aqueous solution was fed therein at a rate of 80 g/min by a peristaltic pump, granulation was continuously carried out for 4 minutes at a screw speed of 700 rpm using the screw structure shown in Table 22. The granulated powder was dried in a fluid bed dryer. 450 g of the dried powder was sized at 1200 rpm using a sizer (brand name: Quadro Comil 197S, Powrex Corporation), with a grater-type screen (mesh size: 1.06 mm) and a compression-type blade. To 396 g of the resulting sized powder, magnesium stearate 4.0 g was added and mixed. For the post-tableting process, FC tablets were obtained in the same manner as in Example 6-(1).

TABLE 22

| Screw structure | XT/6 · N/4 · 60°/1.5T/6 · N/4 · 60°/1.5T/2 · N/6 · 60° |
|---|---|

Example 10: Obeticholic Acid 10 mg FC Tablets (Double Screw Wet Granulation Method)

Obeticholic acid 50.0 g, lactose hydrate 524.0 g, low-substituted hydroxypropyl cellulose 84.0 g, and crospovidone 21.0 g were weighed out and mixed in a plastic bag. The powder mixture was introduced into the powder supply feeder of a double screw wet granulator. The powder mixture was fed at a rate of 20 kg/hour from the powder supply feeder into the chamber, and as 8.5% per weight polyvinyl alcohol aqueous solution was fed therein at a rate of 80 g/min by a peristaltic pump, granulation was continuously carried out for 1.5 minutes at a screw speed of 700 rpm using the screw structure shown in Table 22. The granulated powder was dried in a fluid bed dryer. 455 g of the dried powder was sized at 1200 rpm using a sizer (brand name: Quadro Comil 197S, Powrex Corporation), with a grater-type screen (mesh size: 1.06 mm) and a compression-type blade. To 396 g of the resulting sized powder, magnesium stearate 4.0 g was added and mixed. For the post-tableting process, FC tablets were obtained in the same manner as in Example 6-(1).

Example 11: Obeticholic Acid 10 mg FC Tablets (Double Screw Wet Granulation Method)

Obeticholic acid 50.0 g, lactose hydrate 468.0 g, partly pre-gelatinized starch (Starch 1500: by Colorcon) 140.0 g, and crospovidone 21.0 g were weighed out and mixed in a plastic bag. The powder mixture was introduced into the powder supply feeder of a double screw wet granulator. The powder mixture was fed at a rate of 20 kg/hour from the powder supply feeder into the chamber, and as 13.8% per weight polyvinyl alcohol aqueous solution was fed therein at a rate of 50 g/min by a peristaltic pump, granulation was continuously carried out for 1.5 minutes at a screw speed of 700 rpm using the screw structure shown in Table 22. The granulated powder was dried in a fluid bed dryer, 489 g of the dried powder was sized at 1200 rpm using a sizer (brand name: Quadro Comil 197S, Powrex Corporation), with a grater-type screen (mesh size: 1.06 mm) and a compression-type blade. To 396 g of the resulting sized powder, magnesium stearate 4.0 g was added and mixed. For the post-tableting process, FC tablets were obtained in the same manner as in Example 6-(1).

Table 23 shows the formulations of the obeticholic acid FC tablets obtained in Examples 9 to 11.

<Results>

Evaluation results pertaining to Examples 9 to 11 are shown in Tables 24 and 25.

For comparison, the results of Comparative Example 1 are also shown. The increase in obeticholic acid dimerization observed during storage of obeticholic acid film-coated tablets which used triethyl citrate which is preferred as the specific plasticizer and which were prepared using a double screw wet granulation method was significantly lower compared to Comparative Example 1, wherein polyethylene glycol was used as a plasticizer. In particular, for the FC tablets obtained in Examples 9 to 11, the fact that dimer production was limited to less than 0.5% following storage for 1 M and 3 M at 40° C. and 75% RH (open) represents an excellent result.

TABLE 24

| Amount of obeticholic acid dimer production (%) | | | |
|---|---|---|---|
| | | 40° C, 75% RH. open | |
| | Initial | 1 M | 3 M |
| Comparative Example 1 | 0.25 | 0.57 | 1.55 |
| Example 9 | 0.10 | 0.25 | 0.40 |
| Example 10 | 0.10 | 0.25 | 0.39 |
| Example 11 | 0.10 | 0.23 | 0.39 |

TABLE 23

| | Formulation of obeticholic acid FC tablets | | | |
|---|---|---|---|---|
| | Component | Example 9 | Example 10 | Example 11 |
| Uncoated tablet | Obeticholic acid | 20.0 | 10.0 | 10.0 |
| | Lactose | 94.8 | 104.8 | 93.6 |
| | Partially pre-gelatinized starch | — | — | 28.0 |
| | Low-substituted hydroxypropyl cellulose | 16.8 | 16.8 | — |
| | Crospovidone | 4.2 | 4.2 | 4.2 |
| | Polyvinyl alcohol (partially saponified product) | 2.8 | 2.8 | 2.8 |
| | Magnesium stearate (plant-derived) | 1.4 | 1.4 | 1.4 |
| FC | Hydroxypropylmethyl cellulose | 3.00 | 3.00 | 3.00 |
| | Talc | 0.61 | 0.61 | — |
| | Titanium oxide | 0.24 | 0.24 | 0.85 |
| | Triethyl citrate (plasticizer) | 0.15 | 0.15 | 0.15 |
| | Carnauba wax | Trace amount | Trace amount | Trace amount |
| | Total | 144.0 | 144.0 | 144.0 |

<Storage>

The tablets containing 10 mg or 20 mg of obeticholic acid produced for Examples 9 to 11 were stored under the following conditions. The amounts of obeticholic acid dimer generated before (initial) and after storage were measured in accordance with the methods of Test Examples 1 and 4 respectively.

One month (1 M) and 3 months (3 M) at 40° C. and 75% RH (open)

TABLE 25

| Increase (%) in obeticholic acid dimerization from initial product | | |
|---|---|---|
| | 40° C. 75% RH. open | |
| | 1 M | 3 M |
| Comparative Example 1 | 0.32 | 1.30 |

TABLE 25-continued

Increase (%) in obeticholic acid dimerization from initial product

| | 40° C. 75% RH. open | |
|---|---|---|
| | 1 M | 3 M |
| Example 9 | 0.15 | 0.30 |
| Example 10 | 0.15 | 0.29 |
| Example 11 | 0.13 | 0.29 |

Example 12

In order to obtain basic data to design a preferred formulation of the present invention, the following formulation alteration testing was performed, whereby obeticholic acid and various additives were put into direct contact with each other in order to determine whether or not they promoted proliferation of obeticholic acid dimers which are a readily generated impurity.

<Formulation Alteration Test: Dry Mixing> Obeticholic Acid/Various Additives=1/19

Obeticholic acid/various additives (including an excipient, disintegrant and fluidizing agent; 15 types in total) were thoroughly dried and mixed together at a ratio of 1/19 and the resulting mixture was weighed out into test tubes in approximately 100 mg portions (each equivalent to 5 mg of obeticholic acid) and placed in storage. Two storage conditions were used: 50° C. and 85% RH (open) and 60° C. (closed), and the corresponding storage periods were 2 weeks (2 W) and 4 weeks (4 W). The amounts of obeticholic acid dimer generated were measured in accordance with Test Example 2.

Evaluation results pertaining to Example 12 are shown in Tables 26 and 27. Increases in obeticholic acid dimerization observed following mixing of obeticholic acid and 13 different additives (excipient, disintegrant, fluidizing agent) in Examples 12-(1) to 12-(15) were comparable to obeticholic acid (unmodified) (Comparative Example 3). In other words, none of the additives tested in this example promoted obeticholic acid dimerization.

TABLE 26

Amount of obeticholic acid dimer production (%)

| Example Number | Drug | | Additive | Initial | 50° C., 85% RH, Open, 2 W | 50° C., 85% RH, Open, 4 W | 60° C., Closed, 2 W | 60° C., Closed, 4 W |
|---|---|---|---|---|---|---|---|---|
| Comparative Example 3 | Obeticholic acid | None (unmodified) | — | 0.04 | | 0.83 | | 0.81 |
| Example 12-(1) | | Excipient | Mannitol | 0.04 | | 0.80 | | 0.80 |
| Example 12-(2) | | | Crystalline cellulose | 0.04 | | 0.78 | | 0.89 |
| Example 12-(3) | | | Corn starch | 0.04 | 0.35 | 0.82 | 0.67 | 1.14 |
| Example 12-(4) | | | Lactose | 0.04 | | 0.82 | | 0.90 |
| Example 12-(5) | | | Anhydrous lactose | 0.05 | | 0.81 | | 0.92 |
| Example 12-(6) | | Disintegrant | Partially pre-gelatinized starch | 0.04 | | 0.77 | | 0.99 |
| Example 12-(7) | | | Crospovidone | 0.04 | | 0.52 | | 0.86 |
| Example 12-(8) | | | Sodium carboxymethyl starch | 0.04 | 0.30 | 0.60 | 0.79 | 1.66 |
| Example 12-(9) | | | Carboxymethyl cellulose | 0.03 | | 0.85 | | 0.91 |
| Example 12-(10) | | | Low-substituted hydroxypropyl cellulose | 0.04 | 0.37 | 0.80 | 0.63 | 1.14 |
| Example 12-(11) | | | Sodium croscarmellose | 0.04 | | 0.79 | | 0.92 |
| Example 12-(12) | | Excipient | Calcium hydrogen phosphate | 0.05 | 0.42 | 0.90 | 1.87 | 2.73 |
| Example 12-(13) | | | Anhydrous calcium hydrogen phosphate | 0.04 | | 0.77 | | 0.88 |
| Example 12-(14) | | | Precipitated calcium carbonate | 0.03 | | 0.57 | | 0.68 |
| Example 12-(15) | | Fluidizing agent | Light anhydrous silicic acid | 0.06 | | 0.46 | | 0.85 |

TABLE 27

Increase (%) in obeticholic acid dimerization from initial product

| Example Number | Drug | Additive | | 50° C., 85% RH, Open, 2 W | 50° C., 85% RH, Open, 4 W | 60° C., Closed, 2 W | 60° C., Closed, 4 W |
|---|---|---|---|---|---|---|---|
| Comparative Example 3 | Obeticholic acid | None (unmodified) | — | | 0.79 | | 0.78 |
| Example 12-(1) | | Excipient | Mannitol | | 0.77 | | 0.77 |
| Example 12-(2) | | | Crystalline cellulose | | 0.74 | | 0.85 |
| Example 12-(3) | | | Corn starch | 0.32 | 0.78 | 0.64 | 1.11 |
| Example 12-(4) | | | Lactose | | 0.79 | | 0.86 |
| Example 12-(5) | | | Anhydrous lactose | | 0.76 | | 0.88 |
| Example 12-(6) | | Disintegrant | Partially pre-gelatinized starch | | 0.73 | | 0.96 |
| Example 12-(7) | | | Crospovidone | | 0.49 | | 0.82 |
| Example 12-(8) | | | Sodium carboxymethyl starch | 0.26 | 0.57 | 0.75 | 1.62 |
| Example 12-(9) | | | Carboxymethyl cellulose | | 0.81 | | 0.87 |
| Example 12-(10) | | | Low-substituted hydroxypropyl cellulose | 0.32 | 0.76 | 0.59 | 1.10 |
| Example 12-(11) | | | Sodium croscarmellose | | 0.75 | | 0.88 |
| Example 12-(12) | | Excipient | Calcium hydrogen phosphate | 0.38 | 0.86 | 1.83 | 2.68 |
| Example 12-(13) | | | Anhydrous calcium hydrogen phosphate | | 0.73 | | 0.84 |
| Example 12-(14) | | | Precipitated calcium carbonate | | 0.54 | | 0.65 |
| Example 12-(15) | | Fluidizing agent | Light anhydrous silicic acid | | 0.40 | | 0.79 |

Example 13

In order to obtain basic data to design a preferred formulation of the present invention, the following formulation alteration testing was performed, whereby obeticholic acid and various additives were put into direct contact with each other in the presence of lactose, commonly used as an excipient, in order to determine whether or not they promoted proliferation of obeticholic acid dimers which are a readily generated impurity.

<Formulation Alteration Test: Wet Mixing> Obeticholic acid/excipient (lactose)/various additives=1/19/0.4

Obeticholic acid/excipient (lactose) were thoroughly dry mixed at a ratio of 1/19, various additives (7 binding agents: Examples 13-(2) to 13-(8), 1 surfactant: Example 13-(9), 9 plasticizers: Examples 13-(10) to 13-(18)) which were dissolved or suspended in solution were wet mixed into the resulting mixture such that the ratio of obeticholic acid/excipient/additive was equal to 1/19/0.4. For comparison, a sample to which no additive was added was prepared for Example 13-(1). The wet mixture thus obtained was dried in an incubator (50° C. for 4 hours) and weighed out into test tubes in approximately 102 mg portions (each equivalent to 5 mg of obeticholic acid). Two storage conditions were used: 50° C. and 85% RH (open) and 60° C. (closed), and the storage periods were 2 weeks (2 W) and 4 weeks (4 W). The amounts of obeticholic acid dimer generated were measured in accordance with Test Example 2.

Evaluation results pertaining to Example 13 are shown in Tables 28 and 29. Increases in obeticholic acid dimerization observed following mixing of obeticholic acid and 7 different binders as well as 1 type of surfactant in the presence of lactose, corresponding to Examples 13-(2) to 13-(9) were comparable to Example 13-(1), for which no additives were added (i.e., only obeticholic acid and lactose were included). In other words, none of the binders or surfactant tested in this example promoted obeticholic acid dimerization when lactose was present as an excipient.

On the other hand, the speed of the increase in obeticholic acid dimerization observed following mixing of obeticholic acid and 9 different plasticizers in the presence of lactose, corresponding to Examples 13-(10) to 13-(18) was different. Sorbitan sesquioleate (Example 13-(18)) was comparable to Example 13-(1) wherein no additives were added (i.e., only obeticholic acid and lactose were included), and in the presence of lactose acting as an excipient, it did not promote proliferation of obeticholic acid dimers. However, Macrogol 400 and Macrogol 6000 (Examples 13-(15) and 13-(16)), which are polyethylene glycols significantly promoted an increase in obeticholic acid dimerization in the presence of lactose acting as an excipient compared to Example 13-(1), wherein no additives were added. The degree to which an increase was promoted was the greatest among all excipients tested for the current example, consistent with findings obtained when said agents were used as a plasticizer for the coating layer in FC tablets produced for Comparative Examples 1 and 2 above. Of additional interest is the fact that triacetin (Example 13-(11)), though not as potent as polyethylene glycol (Examples 13-(15) and 13-(16)), did in fact promote obeticholic acid dimer proliferation in the formulation tests described here to a suitable degree. However, the inventors of the present inventor (though unexpectedly based on the results presented here) ascertained that the use of the above as a plasticizer for the coating layer in an FC tablet does not promote proliferation of obeticholic acid dimers, as stated in Example 7 above. Therefore, the inventors of the present invention believe that the threshold value or index which should be used to identify a preferred specific plasticizer for the coating layer of an FC tablet should be a value which is lower than the increase in dimerization observed for polyethylene glycol (Examples 13-(15) and 13-(16)) (e.g., 16-18% after 4 W under closed conditions at 60° C.) and a value which is roughly comparable to the increase in dimerization observed for triacetin (e.g., 10-11% after 4 W under closed conditions at 60° C.). In fact, triethyl citrate, propylene glycol, polyoxyethylene sorbitan monooleate and glyceryl monostearate (Examples 13-(10), 13-(13), 13-(14) and 13-(17)) did not show as pronounced an effect as polyethylene glycol in the formulation testing described here and the effect was even more subtle than triacetin though they did promote an increase in obeticholic acid dimerization (e.g., 3-6% after 4 W under closed conditions at 60° C.), however as described in Examples 2, 4 to 6 and 8 above, when they were used as a plasticizer for the coating layer of an FC tablet they did not promote obeticholic acid dimerization and functioned as a preferred specific plasticizer. On the basis of this index discovered and verified by the inventors of the present invention, it is apparent as decribed that of course sorbitan sesquioleate (Example 13-(18)), which does not promote an increase in dimerization, as well as concentrated glycerin (Example 13-(12)) induced only a very slight increase in obeticholic acid dimerization in the round of formulation tests described here (e.g., 2% after 4 W under closed conditions at 60° C.) and function as preferred specific plasticizers. Additionally, all plasticizers evaluable by those skilled in the art may also function as specific plasticizers, provided they are structurally similar and show similar properties to a plasticizer which can be classified as a preferred specific plasticizer under the formulation testing regime described here and they are structurally dissimilar and show different properties to polyethylene glycol.

TABLE 28

| Amount of obeticholic acid dimer production (%) | | | | | | | | |
|---|---|---|---|---|---|---|---|---|
| Example Number | Drug | Excipient | | Additive | Initial | 50° C., 85% RH, Open, 2 W | 50° C., 85% RH, Open, 4 W | 60° C., closed, 2 W | 60° C., closed, 4 W |
| Example 13-(1) | Obeticholic acid | Lactose | None | — | 0.05 | | 0.84 | | 0.92 |
| Example 13-(2) | | | Binder | Hydroxypropyl cellulose | 0.05 | | 0.68 | | 0.79 |
| Example 13-(3) | | | | Methylcellulose | 0.06 | | 0.72 | | 0.85 |
| Example 13-(4) | | | | Hydroxypropylmethyl cellulose | 0.05 | | 0.62 | | 0.79 |
| Example 13-(5) | | | | Polyvinyl alcohol (partially saponified product) | 0.05 | | 0.79 | | 0.85 |
| Example 13-(6) | | | | Polyvinylpyrrolidone K30 | 0.05 | | 0.63 | | 0.91 |
| Example 13-(7) | | | | Copolvidone | 0.05 | | 0.54 | | 0.81 |
| Example 13-(8) | | | | Corn starch | 0.05 | | 0.80 | | 0.88 |
| Example 13-(9) | | | Surfactant | Sodium lauryl sulfate | 0.04 | | 0.84 | | 0.81 |
| Example 13-(10) | | | Plasticizer | Triethyl citrate | 0.13 | 3.67 | 7.82 | 1.69 | 4.09 |
| Example 13-(11) | | | | Triacetin | 0.09 | 3.08 | 6.57 | 7.92 | 10.49 |
| Example 13-(12) | | | | Concentrated glycerin | 0.05 | 0.52 | 1.15 | 1.41 | 2.46 |
| Example 13-(13) | | | | Propylene glycol | 0.05 | 0.42 | 0.86 | 1.08 | 3.37 |
| Example 13-(14) | | | | Polyoxyethylene sorbitan monooleate (Polysorbate 80) | 0.04 | 3.37 | 6.99 | 3.53 | 5.67 |
| Example 13-(15) | | | | Macrogol 400 (Polyethylene Glycol 400) | 0.10 | 4.23 | 8.41 | 10.29 | 18.34 |
| Example 13-(16) | | | | Macrogol 6000 (Polyethylene Glycol 6000) | 0.07 | 3.17 | 6.61 | 6.96 | 16.07 |
| Example 13-(17) | | | | Glyceryl monostearate | 0.06 | 1.26 | 2.74 | 2.48 | 4.34 |
| Example 13-(18) | | | | Sorbitan sesquioleate | 0.13 | 0.31 | 0.69 | 0.32 | 0.66 |

TABLE 29

| Example Number | Drug | Excipient | Additive | | 50° C., 85% RH, Open, 2 W | 50° C., 85% RH, Open, 4 W | 60° C., closed, 2 W | 60° C., closed, 4 W |
|---|---|---|---|---|---|---|---|---|
| Example 13-(1) | Obeticholic acid | Lactose | Crude product, single substance | — | | 0.79 | | 0.87 |
| Example 13-(2) | | | Binder | Hydroxypropyl cellulose | | 0.63 | | 0.74 |
| Example 13-(3) | | | | Methylcellulose | | 0.67 | | 0.79 |
| Example 13-(4) | | | | Hydroxypropylmethyl cellulose | | 0.58 | | 0.74 |
| Example 13-(5) | | | | Polyvinyl alcohol (partially saponified product) | | 0.73 | | 0.80 |
| Example 13-(6) | | | | Polyvinylpyrrolidone K30 | | 0.58 | | 0.86 |
| Example 13-(7) | | | | Copolvidone | | 0.50 | | 0.76 |
| Example 13-(8) | | | | Corn starch | | 0.75 | | 0.83 |
| Example 13-(9) | | | Surfactant | Sodium lauryl sulfate | | 0.80 | | 0.77 |
| Example 13-(10) | | | Plasticizer | Triethyl citrate | 3.54 | 7.70 | 1.56 | 3.97 |
| Example 13-(11) | | | | Triacetin | 2.99 | 6.48 | 7.83 | 10.41 |
| Example 13-(12) | | | | Concentrated glycerin | 0.47 | 1.10 | 1.35 | 2.41 |
| Example 13-(13) | | | | Propylene glycol | 0.37 | 0.81 | 1.03 | 3.32 |
| Example 13-(14) | | | | Polyoxyethylene sorbitan monooleate (Polysorbate 80) | 3.32 | 6.94 | 3.49 | 5.62 |
| Example 13-(15) | | | | Macrogol 400 (Polyethylene Glycol 400) | 4.13 | 8.30 | 10.18 | 18.23 |
| Example 13-(16) | | | | Macrogol 6000 (Polyethylene Glycol 6000) | 3.10 | 6.54 | 6.89 | 16.00 |
| Example 13-(17) | | | | Glyceryl monostearate | 1.20 | 2.68 | 2.42 | 4.28 |
| Example 13-(18) | | | | Sorbitan sesquioleate | 0.18 | 0.56 | 0.19 | 0.53 |

Increase (%) in obeticholic acid dimerization from initial product

Examples 14 to 22

By replacing the coating material used for the tablet formulation containing obeticholic acid disclosed in Patent Document 2 (specified film-coated tablet) with the material of the invention of this application, it is possible to obtain the film-coated tablet of the invention of the present application. For example, more specifically, based on the disclosure in Patent Document 2 of a tablet that contains 25 mg of obeticholic acid, 157 mg of microcrystalline cellulose, 12 mg of sodium starch glycolate, 2 mg of magnesium stearate, 4 mg of colloidal silicon dioxide, and 8 mg of a coating material (Opadry II) (per tablet), it is possible to apply a coating using the coating formulations shown in Examples 1 to 5, 7 to 8, 9 (or 10) and 11 (note that the amounts may be adjusted as appropriate based on the amounts of obeticholic acid and uncoated tablet used) and the methods described therein to an obeticholic acid 25 mg uncoated tablet which does not include Opadry II, to obtain the FC tablets given in Examples 14 to 22.

Table 30 Shows the Formulations Pertaining to Examples 14 to 22.

TABLE 30

Formulation of obeticholic acid FC tablets (mg)

| | Component | Example 14 | Example 15 | Example 16 | Example 17 | Example 18 | Example 19 | Example 20 | Example 21 | Example 22 |
|---|---|---|---|---|---|---|---|---|---|---|
| Uncoated tablet portion | Obeticholic acid | 25.0 | 25.0 | 25.0 | 25.0 | 25.0 | 25.0 | 25.0 | 25.0 | 25.0 |
| | Microcrystalline cellulose | 157.0 | 157.0 | 157.0 | 157.0 | 157.0 | 157.0 | 157.0 | 157.0 | 157.0 |
| | Sodium starch glycolate | 12.0 | 12.0 | 12.0 | 12.0 | 12.0 | 12.0 | 12.0 | 12.0 | 12.0 |

TABLE 30-continued

Formulation of obeticholic acid FC tablets (mg)

| | Component | Example 14 | Example 15 | Example 16 | Example 17 | Example 18 | Example 19 | Example 20 | Example 21 | Example 22 |
|---|---|---|---|---|---|---|---|---|---|---|
| Coating Portion | Colloidal silicon dioxide | 4.0 | 4.0 | 4.0 | 4.0 | 4.0 | 4.0 | 4.0 | 4.0 | 4.0 |
| | Magnesium stearate | 2.0 | 2.0 | 2.0 | 2.0 | 2.0 | 2.0 | 2.0 | 2.0 | 2.0 |
| | Coating agent containing lecithin as a plasticizer | 8.00 | — | — | — | — | — | — | — | — |
| | Coating agent containing glyceryl monostearate as a plasticizer | — | 8.00 | — | — | — | — | — | — | — |
| | Coating agent not containing plasticizer | — | — | 8.00 | — | — | — | — | — | — |
| | Coating agent containing propylene glycol as a plasticizer | — | — | — | 8.00 | — | — | — | — | — |
| | Hydroxypropylmethyl cellulose | — | — | — | — | 6.00 | 6.00 | 6.00 | 6.00 | 6.00 |
| | Talc | — | — | — | — | 0.70 | — | — | 1.22 | — |
| | Titanium oxide | — | — | — | — | 1.00 | 1.20 | 1.20 | 0.48 | 1.70 |
| | Triacetin | — | — | — | — | — | 0.80 | — | — | — |
| | Polyoxyethylene sorbitan monooleate | — | — | — | — | — | — | 0.80 | — | — |
| | Triethyl citrate | — | — | — | — | 0.30 | — | — | 0.30 | 0.30 |
| | Carnauba wax | — | — | — | — | — | Trace amount | Trace amount | Trace amount | Trace amount |
| Total | | 208.0 | 208.0 | 208.0 | 208.0 | 208.0 | 208.0 | 208.0 | 208.0 | 208.0 |

Equivalent effects can be confirmed by evaluating the FC tablets shown in Examples 14 to 22 in the same manner as in the FC tablets given in Examples 1 to 5 and 7 to 11.

The invention claimed is:

1. A film-coated tablet containing obeticholic acid or a pharmaceutically acceptable salt thereof, comprising:
   (a) an uncoated tablet containing obeticholic acid or a pharmaceutically acceptable salt thereof, and
   (b) a film base on the surface of said uncoated tablet, comprising a coating layer which contains at least one type of specific plasticizer selected from a group consisting of: triethyl citrate, lecithin, glycerin fatty acid ester, propylene glycol, triacetin, polyoxyethylene sorbitan fatty acid ester, concentrated glycerin, sorbitan fatty acid ester, sorbitol, glycerin, diethyl phthalate, dibutyl sebacate, tributyl citrate, diethyl sebacate, acetylated monoglyceride, acetyl triethyl citrate, acetyl tributyl citrate, monostearin dioctyl phthalate, butyl phthalyl butyl glycolate and medium chain fatty acid triglycerides; wherein the plasticizer does not comprise polyethylene glycol.

2. The film-coated tablet of claim 1, wherein the sorbitan fatty acid ester is sorbitan sesquioleate or sorbitan monolaurate.

3. The film-coated tablet of claim 1, wherein the glycerin fatty acid ester is glyceryl monostearate.

4. The film-coated tablet of claim 1, wherein the polyoxyethylene sorbitan fatty acid ester is polyoxyethylene sorbitan monooleate.

5. The film-coated tablet of claim 1, wherein the specific plasticizer is selected from a group consisting of triethyl citrate, propylene glycol and triacetin.

6. The film-coated tablet of claim 1, wherein the specific plasticizer is triethyl citrate.

7. The film-coated tablet of claim 1, wherein the amount of the specific plasticizer included is 0.1 to 30% by weight.

8. The film-coated tablet of claim 1, wherein the coating layer which includes at least one type of the specific plasticizer includes at least one type of film base selected from a group consisting of hydroxypropyl methyl cellulose, hydroxypropyl cellulose, methyl cellulose, ethyl cellulose, polyvinyl alcohol-based resin, polyvinyl pyrrolidone and methacrylic acid copolymer.

9. The film-coated tablet of claim 1, wherein the coating layer which includes at least one type of the specific plasticizer includes at least one type of film base selected from a group consisting of hydroxypropyl methyl cellulose and polyvinyl alcohol-based resin.

10. The film-coated tablet of claim 8, wherein the polyvinyl alcohol-based resin is any of polyvinyl alcohol, a polyvinyl alcohol derivative, a polyvinyl alcohol copolymer or a mixture thereof.

11. The film-coated tablet of claim 8, wherein the polyvinyl alcohol-based resin is polyvinyl alcohol.

12. The film-coated tablet of claim 1, wherein the coating layer which includes at least one type of the specific plasticizer includes a hydroxypropyl methyl cellulose film base.

13. The film-coated tablet of claim 8, wherein the amount of the film base included is 30 to 98% of the coating layer by weight.

* * * * *